US008859990B2

(12) United States Patent
Ng et al.

(10) Patent No.: US 8,859,990 B2
(45) Date of Patent: Oct. 14, 2014

(54) HIGHLY COMPACT MULTI-OPTICAL-JUNCTION OPTICAL FLOWCELL AND FLEXIBLY DEPLOYABLE OPTICAL SENSING ASSEMBLIES AND SYSTEMS FOR IN-SITU REAL-TIME SPECTROSCOPIC MEASUREMENTS

(75) Inventors: Chee Loon Ng, Singapore (SG); Harold F Hemond, Cambridge, MA (US); Schuyler Senft-Grupp, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 14/113,026

(22) PCT Filed: Apr. 20, 2012

(86) PCT No.: PCT/SG2012/000142
§ 371 (c)(1),
(2), (4) Date: Dec. 27, 2013

(87) PCT Pub. No.: WO2012/144955
PCT Pub. Date: Oct. 26, 2012

(65) Prior Publication Data
US 2014/0103224 A1    Apr. 17, 2014

Related U.S. Application Data

(60) Provisional application No. 61/447,661, filed on Feb. 28, 2011, provisional application No. 61/494,014, filed on Jun. 7, 2011, provisional application No. 61/571,593, filed on Jun. 30, 2011.

(51) Int. Cl.
*G01N 21/64* (2006.01)
*G01N 21/01* (2006.01)
*G01N 21/25* (2006.01)

(52) U.S. Cl.
CPC .............. *G01N 21/01* (2013.01); *G01N 21/255* (2013.01); *G01N 21/64* (2013.01)
USPC ...... 250/435; 250/428; 250/459.1; 250/461.1; 356/246; 356/319

(58) Field of Classification Search
CPC ....... G01N 21/64; G01N 21/01; G01N 21/05; G01N 21/255; G01N 21/534; G01N 21/6408; G01N 21/65; G01N 15/1434
USPC ............ 250/428, 435, 459.1, 461.1; 356/246, 356/319
See application file for complete search history.

(56) References Cited

U.S. PATENT DOCUMENTS

| | | | |
|---|---|---|---|
| 8,159,670 B2 * | 4/2012 | Vacca et al. .................... 356/337 |
| 8,400,632 B2 * | 3/2013 | Vacca et al. .................... 356/337 |
| 2009/0142765 A1 * | 6/2009 | Vacca et al. ........................ 435/6 |
| 2012/0270306 A1 * | 10/2012 | Vacca et al. ............... 435/287.2 |
| 2014/0103224 A1 * | 4/2014 | Ng et al. ....................... 250/435 |

* cited by examiner

*Primary Examiner* — David A Vanore
(74) *Attorney, Agent, or Firm* — Ming Chow; Sinorica, LLC

(57) ABSTRACT

A highly compact multi-optical-junction optical flowcell includes a housing having an internal channel, to which a plurality of source optical signal modules can be coupled, e.g., in a peripheral manner. The source optical signal modules can include a set of LEDs and/or semiconductor lasers, and can be coupled to the flowcell by way of a standard optical coupling such as an SMA-type optical connector. An excitation detection apparatus or subsystem can also be coupled to the flowcell to facilitate multiple types of optical measurements, including fluorescence spectroscopy, absorption spectroscopy, and turbidity measurements. A sensing apparatus or system that includes a multi-optical-junction optical flowcell, a plurality of source optical signal modules, and an excitation detection apparatus can be carried by or deployed on a wide variety of platforms, such as Autonomous Underwater Vehicles (AUVs), Autonomous Surface Vehicles (ASVs), buoys, or other platforms, in a space efficient and power efficient manner.

32 Claims, 26 Drawing Sheets

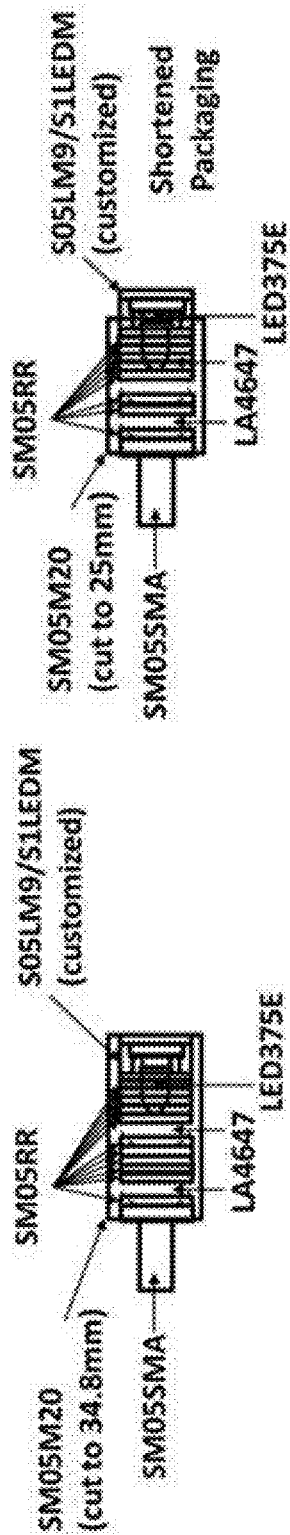
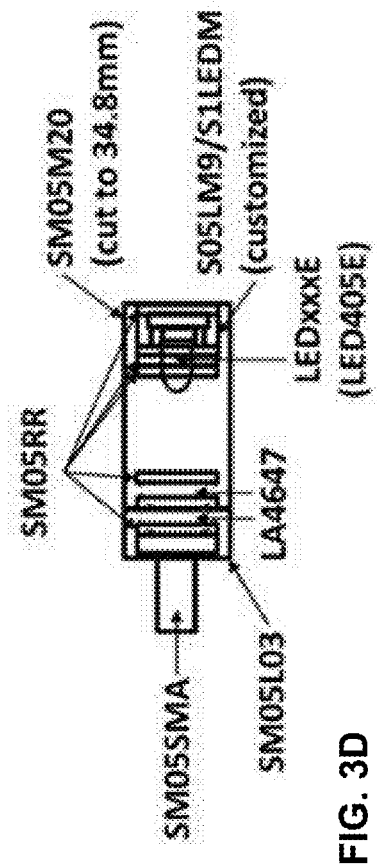
FIG. 3C
FIG. 3D

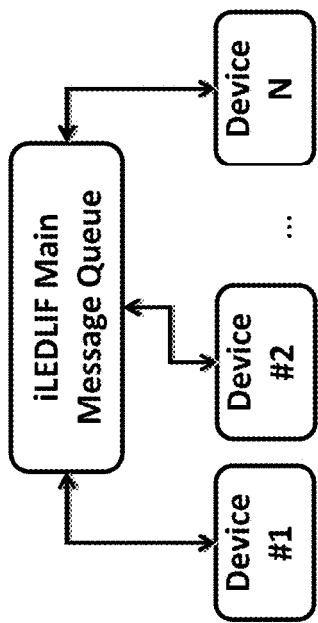

FIG. 10

```
Spec1 SetBoxcar 4                            'This will set the box car of the spectrometer to 4 pixels.
Spec1 SetIntegration 1000                    'This will set the integration time of the spectrometer to 1 second.
LEDArray1 TurnOffLED                         'This will ensure that all LEDs have been turned off.
THIS WAIT ScanComplete Spec1 Scan            'This will wait until the scan finishes before executing the next command.
THIS DO 2                                    'This will repeat the subsequent command loop twice—1st loop.
THIS WAIT LEDon LEDArray1 TurnonLED 1        'This will wait until LED 1 is turned on before executing the next command.
THIS WAIT ScanComplete Spec1 Scan            'This will wait until the scan finishes before executing the next command.
THIS DO 5                                    'This will repeat data acquisition for 5 LED wavelengths—2nd loop.
THIS WAIT LEDon LEDArray1 NextLED            'This will turn on the next (subsequent wavelength, such as 285nm) LED. It will wait
                                              until the LED is on before executing the next command.
THIS WAIT ScanComplete Spec1 Scan            'This will wait until the scan finishes before executing the next command.
THIS LOOP                                    ' End of 2nd loop.
LEDArray1 TurnOffLED                         'This will turn off the LED at the end of the 2nd loop.
THIS LOOP                                    ' End of 1st loop.
```

FIG. 11

HIGHLY COMPACT MULTI-OPTICAL-JUNCTION OPTICAL FLOWCELL AND FLEXIBLY DEPLOYABLE OPTICAL SENSING ASSEMBLIES AND SYSTEMS FOR IN-SITU REAL-TIME SPECTROSCOPIC MEASUREMENTS

TECHNICAL FIELD

The present disclosure relates generally to flowcell-based systems and techniques for performing optical measurements. Particular aspects of the present disclosure are directed to structures, devices, assemblies, apparatuses, systems, and techniques configured for in-situ real-time optical characterization of fluids by way of a highly compact multi-optical-junction flowcell assembly and optical sensing elements, assemblies, and systems configured for performing optical measurements such as such as fluorescence spectroscopy, absorption spectroscopy, and/or turbidity measurements. Various embodiments in accordance with the present disclosure can be readily carried by a wide variety of deployment platforms, such as automated, semi-automated, autonomous, or semi-autonomous platforms, for instance, autonomous underwater vehicles (AUVs), an autonomous surface vehicles (ASVs), or buoys.

BACKGROUND

Current technology for chemical sensing at actionable levels involves costly laboratory instrumentation or expensive field instruments, and provides information over limited spatial extent with often excessive time delay. Existing systems thus tend to be bulky, discrete in nature, location specific, and cost, labor, and time intensive, and are at best inefficiently or ineffectively integrated together, such that they fail to efficiently provide multiple types (such as spectrofluorometry, spectrophotometry, and turbidity) of measurements within a unified or single instrument.

Flowcells are commonly used in spectrofluorometry and spectrophotometry measurements. Commercially available flowcells for spectrofluorometry (fluorescence) measurement usually consist of an excitation optical junction and a detecting optical junction instrumented perpendicular with respect to each other, with the intention to minimize undesirable excitation wavelengths from overlapping with fluorescence wavelengths reaching a detector. On the contrary, spectrophotometry measures the absorbance of the liquid sample in interest; as such, the excitation and detecting optical junctions are instrumented relative to one another with respect to a common or shared axis.

Most commercially available in-situ fluorometers use a single UV excitation source for inducing fluorescence. The setup is favorable in term of sensor packaging and simplicity. However, in the absence of multi-excitation, it does not permit excitation-emission matrix spectroscopy, and also posts limitations to the sensor's ability in separating individual spectra of a complex mixture. For lab-based sensors, the multi-excitation fluorescence measurements have been performed using a single excitation source comprising multiple wavelengths (e.g., Deuterium Tungsten) and a long-pass filter system or a monochrometer to select the wavelength of interest, one at a time, for inducing fluorescence. These added components are usually bulky, heavy, and expensive, rendering an instrument unsuitable for in-situ chemical sensing. Another limitation is that fluorescence and absorbance measurements are seldom made into a single instrument, despite the two differing only in the orientation of the excitation source.

A need exists for fluid sensing or characterization devices, apparatuses, and systems that overcome one or more of the preceding limitations.

SUMMARY

A highly compact (e.g., representative dimensions of ~61 mm in height or length, by ~37 mm in width) multi-optical junction optical flowcell structure in accordance with embodiments of the present disclosure permits concurrent instrumentation of multi-excitation optical systems for both fluorescence and absorbance measurements by way of a single flowcell assembly. Several embodiments in accordance with the present disclosure can utilize multiple low cost LEDs as excitation sources for the construction of an in-situ real-time LED-induced fluorescence (LEDIF) sensor with excitation-emission matrix spectroscopy (EEM spectroscopy or EEMS) capability, which can be carried by or deployed onboard different types of platforms such as AUV, ASV, portable, buoy (stationary or towable), and/or node-based structures, assemblies, apparatuses, or systems. Embodiments in accordance with the present disclosure favor the fabrication of an in-situ optical sensing system having a low fabrication cost.

Multiple embodiments in accordance with the present disclosure can provide an optical platform for performing EEMS procedures on an in-situ optical platform, where the optical platform can perform both fluorescence and absorbance measurements within the same instrument. Excitation and emission spectra are usually broad and do not necessarily require very fine wavelength resolution for multiple practical applications. As such, several embodiments in accordance with the present disclosure include discrete wavelength excitation sources (e.g., LEDs) configured for performing excitation-emission matrix spectroscopy. Coupled with a custom multi-excitation emission optical system that includes a number of source optical signal modules, an optical flowcell in accordance with the present disclosure can carry multiple (e.g., up to twelve) selectable or interchangeable excitation source optical signal modules for performing excitation-emission matrix spectroscopy. The same flowcell is further capable of performing spectrophotometry measurements within the same instrument, allowing self-correction of fluorescence emission measurements due to absorbance.

Multiple embodiments in accordance with the present disclosure can be configured for multi-excitation LED optical (MELO) spectroscopy, which involves discrete wavelength LEDs. Several embodiments are further configured for performing spectrophotometry measurements, thereby facilitating or enabling self-correction of fluorescence emission measurements due to absorbance. Instrumentation can be coupled with a custom designed MELO apparatus or system including (1) various optical layouts to accommodate different (i.e., GaN and ZnO semiconductor gap) LED packages, and (2) a multi-wavelength excitation source for absorbance measurement. To achieve very low detection limits for chemicals where spectrofluorometry is not the conventional approach, flowcell geometries in accordance with embodiments of the present disclosure can accommodate multiple excitation devices, apparatuses, or systems (instrumented perpendicularly relative to a detecting optical junction), which can be activated or turned on concurrently. Consequently, excitation throughput multiplies and hence fluorescence emission increases. By Kasha's rule, the wavelength of fluorescence emission remains unchanged and the excitation wavelength will be dictated by the longest excitation wavelength employed. Optical junctions in accordance with embodiments of the present disclosure can accept optical components corresponding to multiple types of sensors, such as one or both of a LED-Induced Wavelength-Domain Fluorescence sensor and a Laser-Induced Time-Resolved Fluorescence Sensor with Raman Spectroscopy Capabilities.

Multiple embodiments in accordance with the present disclosure include a plurality of source optical signal modules, each of which carries a number of optical signal generation devices such as a set of LEDs and/or a set of semiconductor lasers. For instance, some embodiments can include a series of ultra-compact (~Φ½", ranging from ~1" to 2"(L)) optical systems capable of optimizing the throughput of commercially available low cost LEDs of different package configurations (such as TO-39, HS (heterostructures) on InGaN substrate, among others) for inducing fluorescence, and the coupling of a collective lens with a bundle array patch (or a single core) fiber for the collection of emission signals.

Optical devices, apparatuses, subsystems, and/or systems in accordance with embodiments of the present disclosure are arranged to provide enhanced or optimized excitation throughput for inducing fluorescence and emission collection, based on highly compact (e.g., ultra-compact) flowcell geometry and layout. Nonetheless, such optical systems can be utilized in essentially any type of flowcell geometry, employing built-in adjustment capabilities provided by each optical system, to tailor the optical properties to a given type of flowcell geometry under consideration.

When coupled or instrumented to an optical flowcell that includes multiple optical junctions, embodiments in accordance with the present disclosure can form portions of an in-situ real-time excitation-emission matrix spectrofluorometer that is deployable onboard multiple types of platforms in which optimum optical throughput in ultra-compact packaging or an ultra-compact profile is of high priority (e.g, in AUV, ASV, portable, buoy (stationary/displaceable/movable/towable), node-based, or other types of platforms). For instance, a low cost real-time highly compact (e.g., 200 (Φ)×300 mm (L)) multi-platform (e.g., AUV, ASV, boat side, buoy, or water distribution network) deployable optical spectroscopic sensor in accordance with an embodiment of the present disclosure can be configured for performing (i) fluorescence; (ii) absorbance; and (iii) turbidity measurements within a single self-powered instrument for in-situ universal non-volatile (and several species of volatile) sensing of fluid (e.g., water) chemistry. A sensor in accordance with an embodiment of the present disclosure can detect, measure, or characterize several species of volatile compounds such as BTEX—Benzene, Toluene, Ethylbenzene, and xylenes) in natural waters and marine environments. Compounds detectable by fluorescence spectroscopy include (1) algae blooms; (2) chlorination in water filtration plants; (3) photochemistry; (4) natural (humic) and artificial tracers (such as Fluorescein and Rhodamine); (5) high molecular weight compounds (such as oil); and (6) low molecular weight compounds (such as BTEX), among others. Various compounds are additionally or alternatively detectable by way of absorption-based measurement (as absorbance measurement intensity varies from absorbance in the presence of dispersion, and turbidity provides a mean for correction).

Such a sensor is capable of performing multi-excitation fluorescence measurements and broadband (e.g., 185-1100 nm) absorbance measurements, for providing an in-situ absorbance-corrected excitation-emission matrix fluorescence spectrum for water chemistry research and monitoring, ranging from limnology and oceanography research to the monitoring of water supply and distribution networks due to accidental/unintentional contaminations or experimental/test substance introduction and monitoring. Turbidity measurement is based on Nephelometry principles that are relevant to particle suspension measurement as well as turbidimetric (turbidometric) measurement of bacterial density.

Various embodiments in accordance with the present disclosure include a customized inlet system coupled or couplable to a flowcell, thereby allowing a flowcell to effectively or efficiently draw in a liquid sample by simply relying on the forward motion of a device, apparatus, system, or platform (e.g., an AUV) that carries the flowcell and optical modules, components, or elements coupled thereto, avoiding or eliminating the need for a pump to draw in liquid, and additionally reducing or minimizing power consumption (e.g., onboard an AUV).

An optical spectroscopic chemical sensing apparatus or system in accordance with an embodiment of the present disclosure can detect, sense, or characterize non-volatile compounds, dissolved organic materials, high molecular weight hydrocarbons, pesticides, pigments (such as Chlorophyll), and tracers, for instance, to address a broad range of water quality issues. Such a system can be configured to provide tri-measurement (multi-excitation fluorescence, broadband (e.g., 185-1100 nm) absorbance, and turbidity) capabilities, providing a manner of obtaining absorbance-corrected fluorescence spectra and suspended materials/turbidimetric (turbidometric) measurement of bacterial density with a single sensor module.

Multi-excitation fluorescence measurement devices, apparatuses, and systems in accordance with embodiments of the present disclosure can be configured for excitation-emission matrix spectroscopy, and can generate measurement results comparable to a lab-based broadband excitation fluorometer. Embodiments in accordance with the present disclosure can deliver real-time multi-spectral data where time lag depends on the selected integration time.

Several embodiments in accordance with the present disclosure provide all-in-one packaging including (i) a multiple-optical-junction flowcell; (ii) a series of optical systems for optical enhancement; (iii) a data logging system; (iv) onboard powerboard and computer; and (v) a power source (e.g., a battery). Such all-in-one packaging can correspond to a housing or enclosure having a highly compact cylindrical or other type of shape.

Multi-platform compatible deployment can involve (i) autonomous underwater vehicle (AUV); (ii) autonomous surface vehicle (ASV); (iii) boat side (iv) buoy; (v) node-based host; and/or (vi) other type of deployment. Various embodiments exhibit low cost with minimal maintenance, and are hence well suited for long-term deployment on buoys and multi-node water supply and distribution monitoring networks.

Low power consumption and efficient power management is provided by a power board controlled by software or a program instruction development and execution environment that favors in-situ autonomous vehicle deployment. In addition, field sample feeding into the through flowcell does not require a pump (e.g., a pump can be optional, or entirely excluded/avoided), which further enhances power saving, such as onboard a remotely operated or autonomous vehicle or other type of platform for which power consumption is an important consideration. Furthermore, various embodiments exhibit low cost with minimal maintenance, and are hence well suited for long-term deployment, such as on buoys or multi-node water supply/distribution monitoring networks.

In accordance with an aspect of the present disclosure, an optical flowcell assembly includes a housing having an axial extent, a transverse extent, a periphery, and an internal channel having a length extending along a portion of the housing's axial extent, parallel to an optical signal detection axis of the flowcell assembly; at least one fluid inlet configured for fluid communication with the internal channel; at least one fluid outlet configured for fluid communication with the internal channel; a plurality of transverse optical junctions configured for directing optical signals into the internal channel along an optical signal propagation path that is offset from the flowcell assembly's optical signal detection axis; and at least one axial optical junction configured for receiving optical signals propagating from the internal channel to the at least one axial optical junction. The optical flowcell assembly can also include an axial optical junction configured for directing optical signals into the internal channel along an optical signal propagation path that is substantially parallel to the optical flowcell assembly's optical signal detection axis. A set of optical fibers and/or other optical elements can be optically coupled to one or more axial optical junctions.

The plurality of transverse optical junctions can be configured for directing optical signals into the internal channel along an optical signal propagation path that is substantially transverse to the flowcell assembly's optical signal detection axis. The plurality of transverse optical junctions is configured for optical coupling to a plurality of source optical signal modules, for instance, by way of a first set of transverse optical junctions disposed at a first position relative to the housing's axial extent. The plurality of transverse optical junctions can further include a second set of transverse optical junctions disposed at a second position relative to the housing's axial extent, the first position and the second position spatially offset from each other. At least one of the plurality of transverse optical junctions and one or more axial optical junction can include a first portion of a standard optical connector, such as a miniature (e.g., SMA-type) optical connector.

The optical flowcell assembly can further include a plurality of source optical signal modules, each source optical signal module within the plurality of optical signal modules one of coupled to and carrying one of a set of LEDs and a set of semiconductor lasers. Each source optical signal module can carry one of a single LED and a single semiconductor laser. In some embodiments, one or more source optical signal modules includes a single LED configured for outputting optical signals having a single optical center wavelength or a single LED configured for outputting optical signals having multiple distinct optical center wavelengths.

An optical flowcell assembly in accordance with an embodiment of the present disclosure can be configured for enabling at least two of fluorescence spectroscopy measurements, absorption spectroscopy measurements, and turbidity measurements. In several embodiments, an optical flowcell assembly can be configured for performing EEMS procedures or measurements.

In various embodiments, the optical flowcell assembly is sized and dimensioned for deployment on a platform such as a Remotely Operated Vehicle (ROV), an Autonomous Underwater Vehicle (AUV), an Autonomous Surface Vehicle (ASV), a buoy, and/or a water distribution network, and wherein the optical flowcell assembly facilitates optical spectroscopy measurements by the platform (e.g., which otherwise has much more limited or no optical spectroscopy measurement capabilities).

In accordance with another aspect of the present disclosure, a source optical signal module having an optical axis is optically couplable to an optical flowcell of an optical spectroscopy system, and includes a first portion of an optical connector aligned relative to the optical axis of the source optical signal module and configured for mating engagement with a corresponding second portion of an optical connector separate from the source optical signal module; a housing having an axial extent, an outer cross-sectional area, and an inner cross-sectional area; a set of optical signal sources comprising one of an LED and a semiconductor laser carried internal to the housing, the set of optical signal sources configured to direct optical signals along the optical axis of the source optical signal module; and a set of optical path tuning elements carried internal to the housing and disposed between an optical signal source within the set of optical signal sources and the first portion of the optical connector, the set of optical path tuning elements comprising at least one of a set of lens elements and a set of spacer elements, each optical path tuning element within the set of optical path tuning elements having a cross-sectional area that is transverse to the optical axis of the source optical signal module, each optical path tuning element within the set of optical path tuning elements configured for selective adjustment of an optical path length corresponding to the set of optical signal sources relative to an optical spectroscopy measurement location within the optical flowcell.

A housing of the source optical signal module can have an internal diameter configured to accommodate an LED or a semiconductor laser package in a minimal amount of space. For instance, a housing can have an inner diameter that is less than approximately 2 or 3 times larger than a cross-sectional area of a package corresponding to an LED or a semiconductor laser.

In accordance with a further aspect of the present disclosure, a spectroscopy system includes a flowcell assembly having an axial extent, the flowcell assembly having a fluid inlet structure configured for receiving a fluid; a fluid outlet structure configured for outputting a fluid; a channel internal to the flowcell, the channel having a longitudinal extent configured for providing a spectroscopy measurement region along a fluid communication path between the fluid inlet structure and the fluid outlet structure; a set of transverse optical junctions configured for directing optical signals into the channel substantially transverse to the longitudinal extent of the channel; and an axial optical junction configured for receiving optical signals propagating away from the spectroscopy measurement region in a direction substantially parallel to the longitudinal extent of the channel. The spectroscopy system further includes a set of source optical signal modules physically and optically coupled to the flowcell assembly by way of a set of miniature optical connectors; an emission collection assembly comprising a set of optical fibers optically coupled to the flowcell assembly; and a miniature spectrophotometer optically coupled to the emission collection assembly. Each element of the spectroscopy system can be carried by or reside within a housing, such that the spectroscopy system is a substantially or entirely self-contained system that can be deployed in-situ for real-time fluid characterization by way of spectroscopic measurements. For instance, the spectroscopy system can be configured for performing at least two of fluorescence spectroscopy measurements, absorption spectroscopy measurements, and turbidity measurements. In various embodiments, the spectroscopy system is configured for performing EEMS procedures or measurements.

A spectroscopy system can be configured for performing in-situ real-time spectroscopy measurements by way of directing optical signals provided by the set of source optical signal modules into the optical flowcell assembly's spectroscopy measurement region (e.g., on a sequential or simultaneous basis); capturing optical signals propagating toward the axial optical junction; and providing captured optical signals to the spectrophotometer.

The spectroscopy system can further include a flow transportation manifold coupled to the optical flowcell assembly, the flow transportation manifold configured for in-situ real-time capture of fluid samples from a fluid environment and return of captured fluid samples to the fluid environment. Such a flow manifold facilitates or enables the exclusion of a pump configured for transferring fluid into the optical flowcell assembly. Various embodiments of the spectroscopy system are deployable as a substantially self-contained unit on a plurality of platforms configured for at least partial exposure to fluid environments, where representative platform types include an ROV, an AUV, an ASV, a bouy, and a water distribution network.

The spectroscopy system can additionally include an instruction processing device configured for executing program instruction sets; a memory coupled to the instruction processing device; and a software user interface configured for the generation of program scripts as text files specifying a set of commands written in accordance with a scripting language.

In accordance with another aspect of the present disclosure, a process for performing optical spectroscopy measurements by way of a substantially self-contained optical spectroscopy system configured for in-situ real-time optical spectroscopy measurements includes deploying at least a portion of the substantially self-contained spectroscopy system in-situ within a fluid environment; receiving a fluid sample within an internal channel of an optical flowcell assembly of the spectroscopy system; and performing excitation-emission matrix spectroscopy measurements by way of: energizing one of a set of LEDs and a set of semiconductor lasers carried by the spectroscopy system to generate a plurality optical excitation signals, each optical excitation signal within the plurality of optical excitation signals having a distinct optical center wavelength; directing the plurality of optical excitation signals into the internal channel of the flowcell assembly (e.g., on a sequenced or simultaneous basis); detecting a set of optical emission signals corresponding to the plurality optical excitation signals directed into the internal channel of the flowcell; and performing a set of fluorescence spectroscopy measurements.

BRIEF DESCRIPTION OF THE DRAWINGS

FIGS. 3C and 3D are schematic illustrations of a representative implementation of a source optical signal module configured for providing a wide half view angle and a narrow half view angle, respectively, for a second type of optical signal source in accordance with an embodiment of the present disclosure.

FIG. 10 shows an iLEDLIF source code process in accordance with a representative embodiment of the present disclosure.

FIG. 11 shows a representative example of a user generated program in accordance with an embodiment of the present disclosure.

DETAILED DESCRIPTION

Figure 1A:
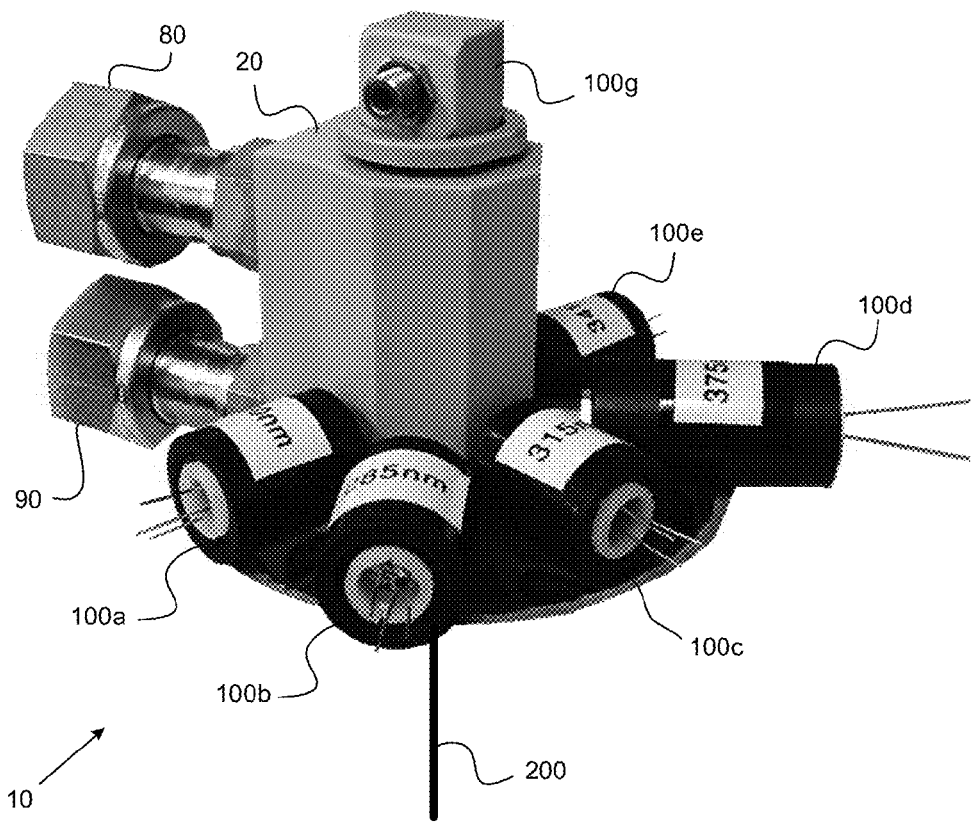
FIG. 1A is a perspective view of a multi-optical-junction optical flowcell assembly in accordance with a representative embodiment of the present disclosure.

In the present disclosure, the depiction of a given element or consideration or use of a particular element number in a particular FIG. or a reference thereto in corresponding descriptive material can encompass the same, an equivalent, or an analogous element or element number identified in another FIG. or descriptive material associated therewith. The use of "/" in the description herein implies "and/or" unless specifically indicated otherwise. Additionally, unless explicitly stated otherwise, in the description herein, the recitation of particular numerical values or value ranges is taken to be a recitation of particular approximate numerical values or approximate value ranges.

As used herein, the term "set" corresponds to or is defined as a non-empty finite organization of elements that mathematically exhibits a cardinality of at least 1 (i.e., a set as defined herein can correspond to a singlet or single element set, or a multiple element set), in accordance with known mathematical definitions (for instance, in a manner corresponding to that described in *An Introduction to Mathematical Reasoning: Numbers, Sets, and Functions*, "Chapter 11: Properties of Finite Sets" (e.g., as indicated on p. 140), by Peter J. Eccles, Cambridge University Press (1998)). In general, an element of a set can include or be a system, an apparatus, a device, a structure, a structural feature, an object, a process, a physical parameter, or a value depending upon the type of set under consideration.

As further detailed herein, embodiments in accordance with the present disclosure are directed to structures, devices, assemblies, apparatuses, systems, and techniques configured for optically sensing, detecting, measuring, monitoring, characterizing, evaluating, and/or analyzing (hereafter "characterizing" for purpose of simplicity and to aid understanding) one or more properties (e.g., compositional or chemical constituent properties) of fluids by way of (1) a highly compact multi-optical-junction flowcell assembly; and/or (2) optical signal provision and optical sensing elements, assemblies, units, modules, apparatuses, subsystems, and systems that can be selectively configured for performing particular types of optical measurements, such as one or more of (e.g., at least two of) fluorescence spectroscopy, absorption spectroscopy, turbidity, and/or other types of measurements. Depending upon embodiment details, a given optical signal provision modules can include optical signal sources configured to provide optical signals having (a) a particular center wavelength; (b) a plurality of center wavelengths (e.g., on a selectable basis, such as by way of a multi-wavelength LED); or wideband or broadband optical wavelengths.

In the context of the present disclosure, the term "fluid" encompasses liquid as well as gaseous media. Thus, particular embodiments in accordance with the present disclosure can be configured for facilitating or performing optical measurements upon liquids, and certain embodiments in accordance with the present disclosure can be configured for facilitating or performing optical measurements upon gases and/or mixtures of gases and liquids (e.g., liquid droplets and/or aerosols in atmospheric environment).

Embodiments in accordance with the present disclosure facilitate or enable real-time optical characterization of fluids on an in-situ basis. Various embodiments facilitate or enable real-time optical characterization of fluids that exist within a source, original, typical, normal, or natural environment corresponding to a body of water (e.g., an ocean, a sea, a lake, a pond, a marsh, a river, an estuary, or other body of water) or a water guiding structure (e.g., a canal). Fluid samples or specimens can flow (a) into the aforementioned flowcell assembly (e.g., on a progressive or continuous basis) to facilitate fluid sample optical characterization; and (b) out of the flowcell assembly, back to an environment from which the fluid sample(s) or specimen(s) originated.

Various embodiments in accordance with the present disclosure are additionally directed to highly space efficient (e.g., ultra-compact) and power efficient in-situ real-time optical measurement apparatuses and systems, such as optical spectroscopy systems, which can be readily carried by or deployed on (e.g., as at least substantially self-contained units) a wide variety of stationary, displaceable, transportable, movable, or mobile platforms that can be disposed proximate to or at least partially within fluid environments. In a number of embodiments, such platforms can include automated, semi-automated, autonomous, or semi-autonomous platforms such aquatic remotely operated vehicles (ROVs), autonomous underwater vehicles (AUVs), autonomous surface vehicles (ASVs), or buoys. Any given platform that carries a spectroscopic measurement apparatus or system in accordance with an embodiment of the present disclosure becomes configured for performing in-situ real-time spectroscopy measurements upon fluids within a platform deployment environment.

Aspects of Representative Multi-Optical-Junction Optical Flowcell Assemblies

FIG. 1A is a perspective view of a multi-optical-junction optical flowcell assembly 10 (hereafter "flowcell" for purpose of simplicity and to aid understanding) in accordance with a representative embodiment of the present disclosure. In an embodiment, the flowcell 10 includes a housing 20 having (a) a height or axial/longitudinal/vertical extent; (b) a cross-sectional or transverse profile, area, or extent; and (c) a periphery that defines a set of exterior or external surfaces. As further detailed below, the housing 20 includes an interior or internal channel, passage, or chamber having a length or longitudinal extent that runs along or parallel to a portion of the housing's height. The housing 20 can include or be fabricated from one or more types of material that are resistive to degradation (e.g., corresponding to chemical, thermal, or corrosive degradation) that can occur or which would be expected in a type of fluid environment under consideration. For instance, the housing can include or be fabricated from stainless steel, or a chemically and/or thermally resistant polymer, for instance, polyether ether ketone (PEEK) or another type of polymer material.

The flowcell 10 includes at least one fluid input or inlet coupling, assembly, fixture 80, and at least one fluid output or outlet coupling, assembly, or fixture 90. Any given fluid inlet assembly 80 and any given fluid outlet assembly 90 is configured for fluid communication with the flowcell's internal channel (e.g., by way of corresponding ports or openings in the housing 20), such that fluid within a fluid environment external to the housing 10 can flow into a fluid inlet assembly 80, into and through the flowcell's internal channel, and out of a fluid outlet assembly 90 back into the fluid environment. A fluid inlet assembly 80 and/or a fluid outlet assembly 90 can include one or more types of fittings or connector elements, such as standard Swagelok (e.g., Male SAE/MS) connectors.

In various embodiments, the housing 20 can be a single, unitary, or substantially unitary piece of material. In some embodiments, the housing 20 can include multiple couplable, engageable (e.g., matingly engageable), or connectable portions, sections, segments, or members, such as an upper portion and a lower portion that can be screwed together (e.g., and which can facilitate selective positioning of the fluid inlet assembly 80 relative to the fluid outlet assembly 90).

In various embodiments such as those further described below, for purpose of simplicity and to aid understanding the flowcell 10 includes a single fluid inlet assembly 80 and a single fluid outlet assembly 90 carried by or coupled to the housing 20. In certain embodiments, the flowcell 20 can include multiple fluid inlet assemblies 80, and/or multiple fluid outlet assemblies 90. Depending upon embodiment details, a fluid inlet assembly 80 and/or a fluid outlet assembly 90 can provide unobstructed, uninterrupted, or continuously open fluid communication pathways; or selectively or switchably accessible, obstructable, closable, or sealable fluid communication pathways relative to the flowcell's internal channel. Embodiments that provide selectively accessible, obstructable, closable, or sealable fluid communication pathways can include or be coupled to a set of actuatable valves, such as solenoid valve assemblies (e.g., which can be mini-scale or micro-scale solenoid valves, depending upon flowcell size), in a manner understood by one of ordinary skill in the relevant art.

The flowcell 10 additionally includes a plurality of optical junction structures or elements as also detailed below, configured for enabling the transfer of optical signals into the flowcell's internal channel from (a) one or more optical signal provision or source optical signal elements, structures, devices, units, modules, or assemblies 100a-e (e.g., fluorescence spectroscopy optical signal sources) configured for directing optical signals into the flowcell's internal channel in a direction offset from, non-parallel to, or at least substantially transverse to the internal channel's length; and possibly (b) an additional source optical signal element, structure, device, unit, module, or assembly 100g (e.g., an absorption spectroscopy optical signal source) configured for directing optical signals into the flowcell's internal channel in a direction aligned with, along, or at least substantially parallel to the internal channel. The additional source optical signal module 100g can include or correspond to an end cap structure that can be selectively secured or mounted to the flowcell 10.

The flowcell 10 further includes a set of optical junction structures or elements configured for facilitating or enabling the transfer of optical signals from the flowcell's internal channel to an optical signal receiving, collection, sensing, or detection element, device, apparatus, assembly, or system 200, for instance, which includes a set of optical fibers configured for optically coupling to an LED and/or laser-induced fluorescence sensor such as a spectrometer such as an Ocean Optics miniature spectrometer (Ocean Optics, Inc., Dunedin, Fla. USA, www.oceanoptics.com).

Figure 1B:
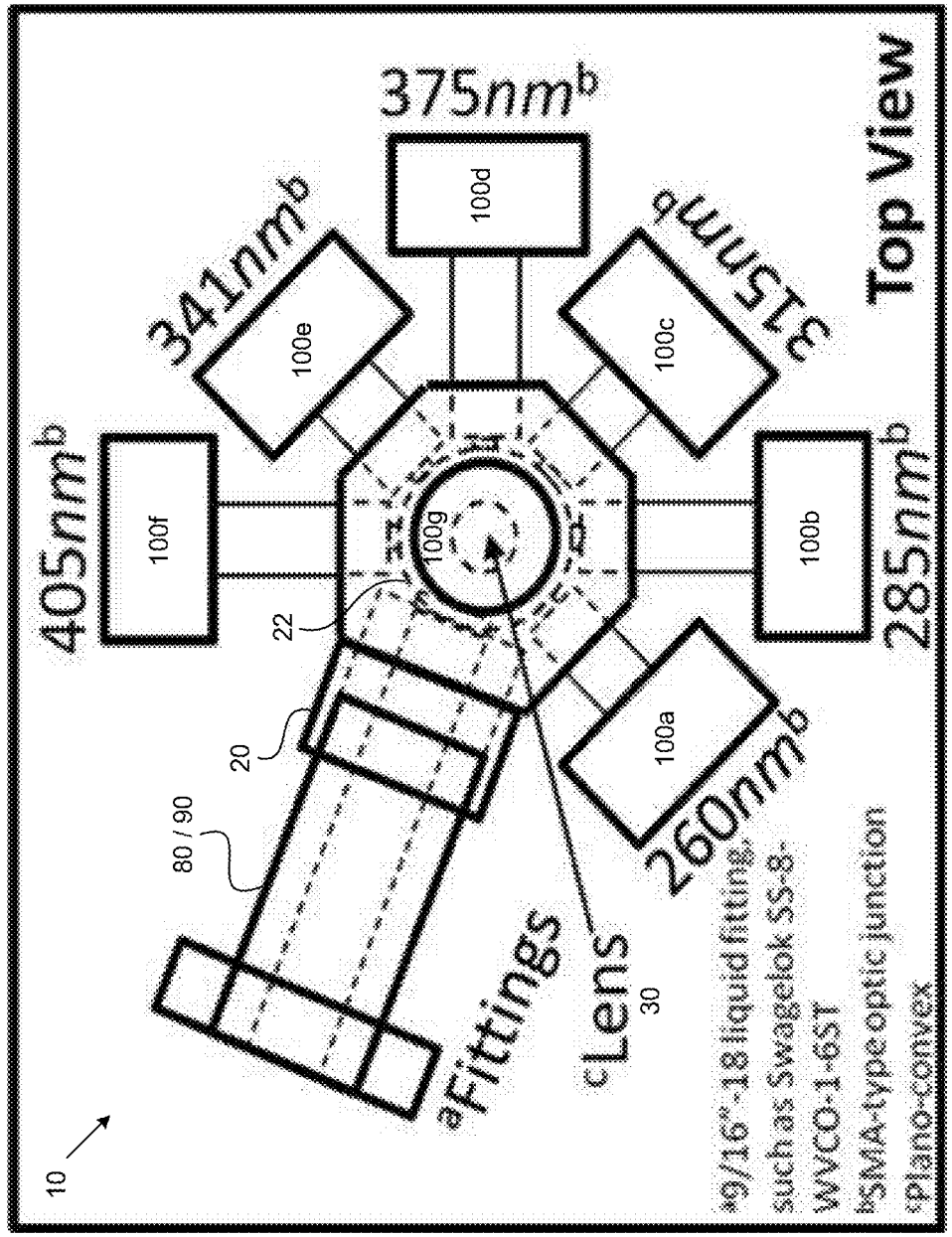
FIG. 1B is a first top cross-sectional schematic illustration of the multi-optical junction flowcell assembly of FIG. 1A.
Figure 1C:
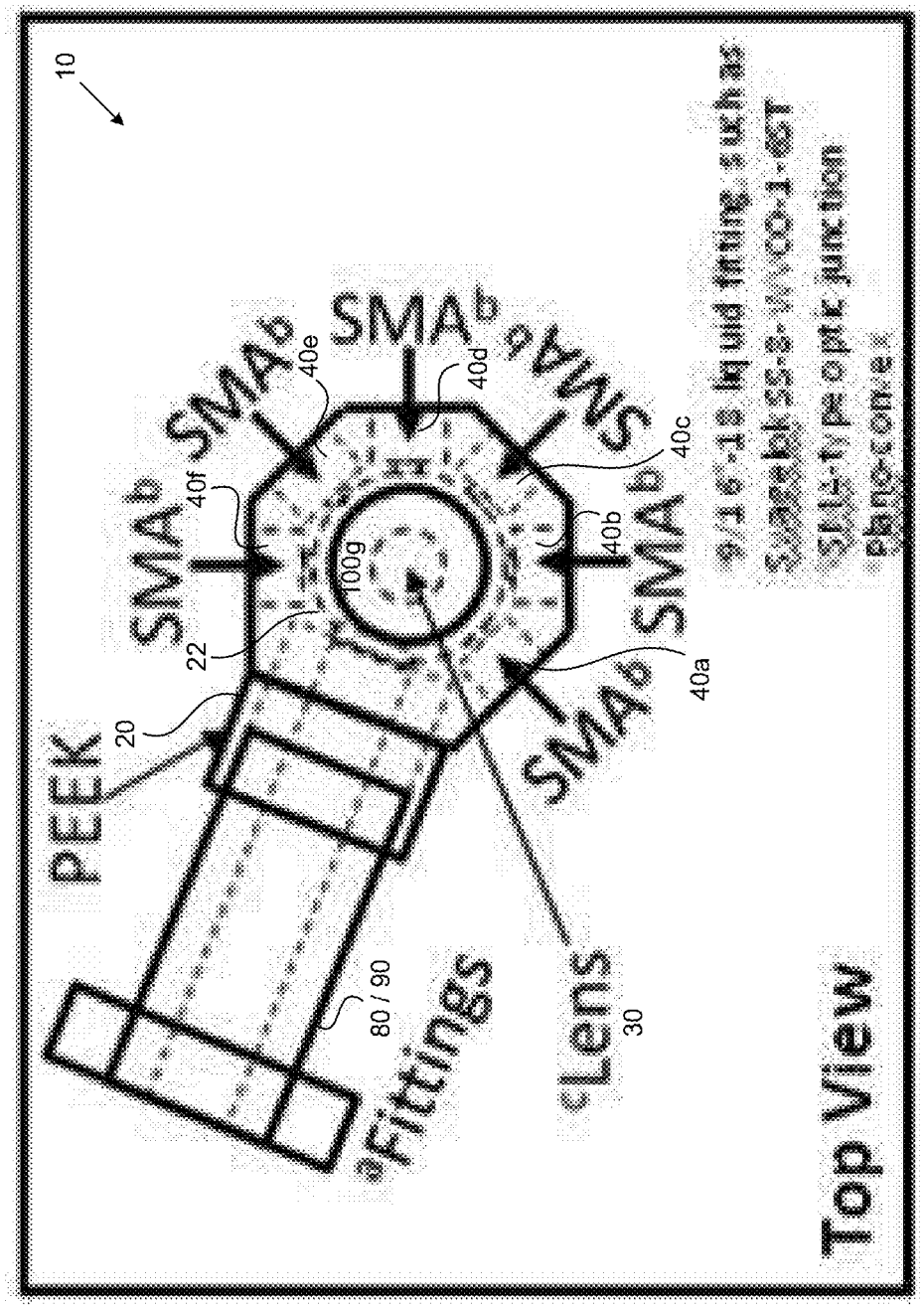
FIG. 1C is a second top cross-sectional schematic illustration of the multi-optical-junction flowcell assembly of FIG. 1A.
Figure 1D:
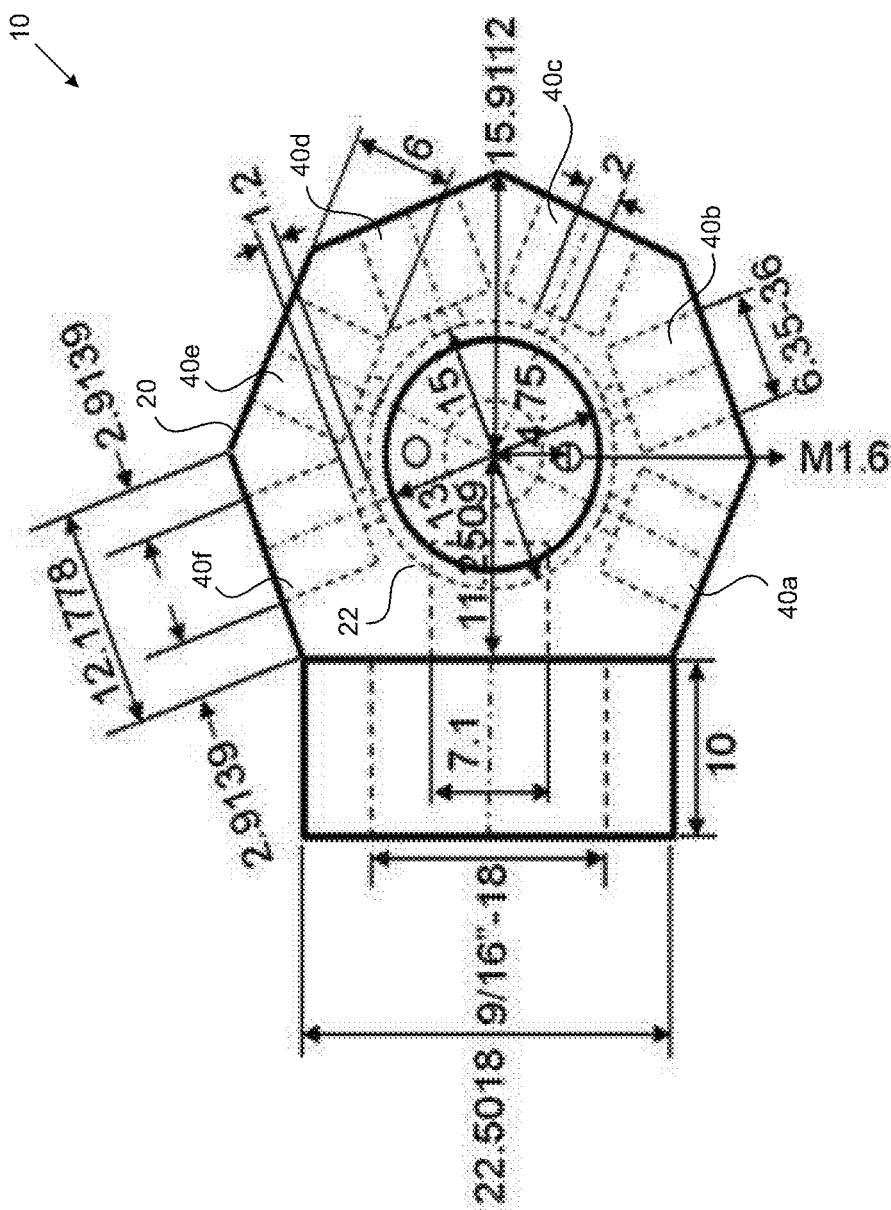
FIG. 1D is a third top cross-sectional schematic illustration of the multi-optical-junction flowcell assembly of FIG. 1A.
Figure 1E:
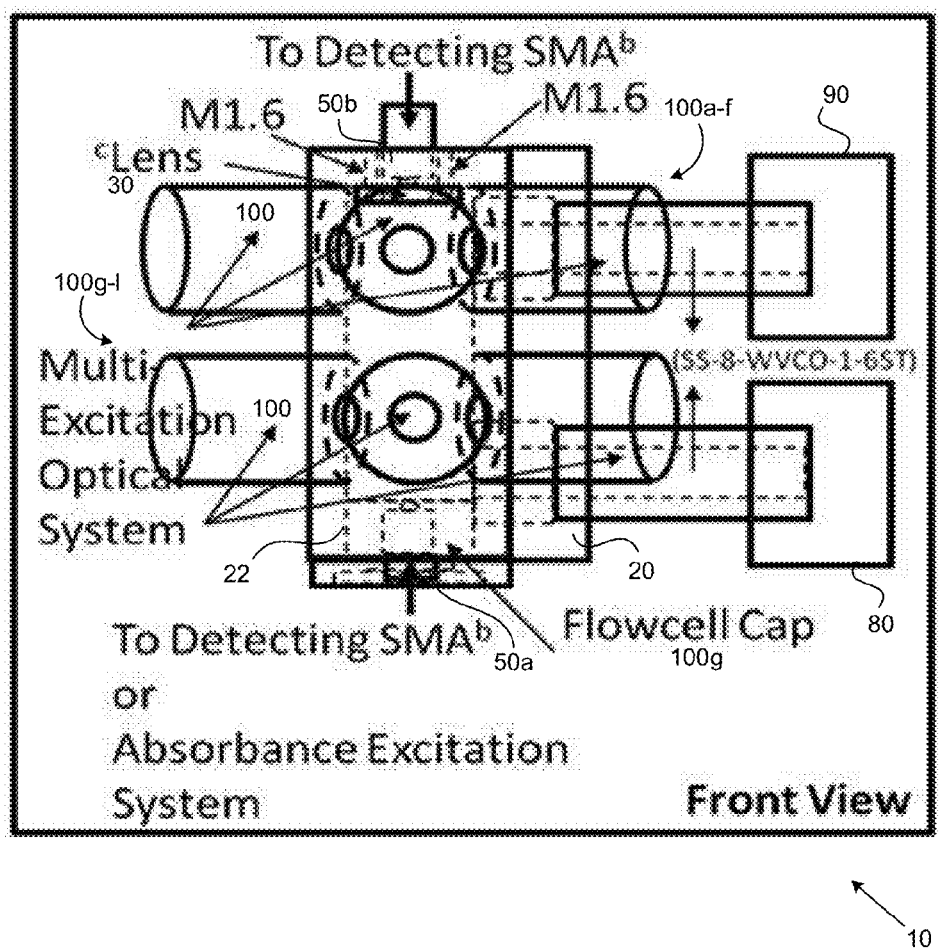
FIG. 1E is a first front schematic illustration of an embodiment of a multi-optical-junction flowcell in accordance with an embodiment of the present disclosure, such as the multi-optical-junction flowcell assembly of FIG. 1A.
Figure 1F:
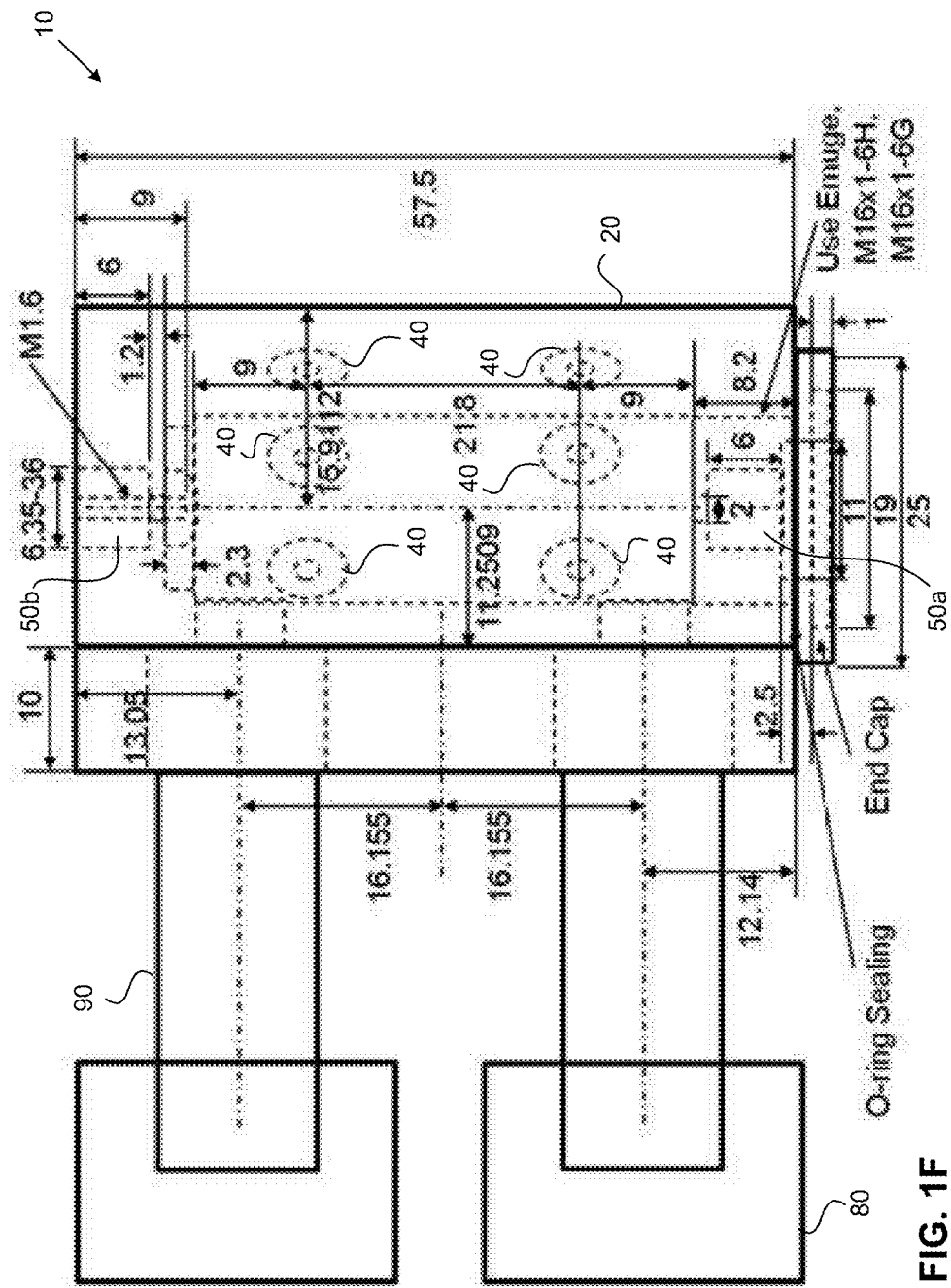
FIG. 1F is a second front schematic illustration of an embodiment of a multi-optical-junction flowcell in accordance with an embodiment of the present disclosure, such as the multi-optical-junction flowcell assembly of FIG. 1A.

FIG. 1B is a first top cross-sectional schematic illustration of the flowcell 10 of FIG. 1A; FIG. 1C is a second top cross-sectional schematic illustration of the flowcell 10 of FIG. 1A; FIG. 1D is a third top cross-sectional schematic illustration of the flowcell 10 of FIG. 1A, which shows particular representative dimensions of a flowcell 10 in millimeters (mm); FIG. 1E is a first front schematic illustration of an embodiment of a flowcell 10 such as that shown in FIG. 1A; and FIG. 1F is a second front schematic illustration of an embodiment of a flowcell 10 such as that shown in FIG. 1A, which shows particular representative flowcell dimensions in mm.

In various embodiments, the flowcell 10 includes a plurality of (e.g., six) transverse optical junctions 40 disposed relative to the periphery of the housing 20 (e.g., disposed about the housing 20 in a circumferential or generally circumferential manner), where each transverse optical junction 40 is configured for providing an optical signal propagation path and/or an optical axis that is substantially transverse to the longitudinal extent of the housing's internal channel 22. A flowcell 10 corresponding to FIGS. 1A-1F can correspondingly accommodate a plurality of (e.g., six) source optical signal modules 100 (e.g., configured for providing, generating, or outputting optical signals corresponding to a plurality of distinct center wavelengths), each of which can be coupled to a corresponding transverse optical junction 40 such that it can be disposed at a given (e.g., predetermined) position or location relative to the housing's periphery and/or height. In a representative implementation, six source optical signal modules 100 can be configured for providing, generating, or outputting optical signals characterized by optical wavelengths (e.g., center wavelengths) of 260 nm, 285 nm, 315 nm, 341 nm, 375 nm, and 405 nm. Other implementations can include additional or other source optical signal modules 100 configured for providing, generating, or outputting optical signals characterized by one or more other optical wavelengths (e.g., center wavelengths).

Some embodiments include a single layer of transverse optical junctions 40 defined relative to a given vertical position along the height of the housing 20, while other embodiments can include multiple layers of transverse optical junctions 40 defined relative to multiple vertical positions or offsets along housing's height. That is, each distinct layer of transverse optical junctions 40 corresponds to a particular vertical position, distance, or offset along the housing's height. For instance, a plurality of transverse optical junctions 40 can include (a) a first set of transverse optical junctions 40a-f disposed at a first vertical position relative to the height of the housing 20; and possibly (b) a second set of transverse optical junctions 40g-l disposed at a second vertical position relative to the height of the housing 20, such that the first set of transverse optical junctions 40a-f corresponds to a first layer of transverse optical junctions 40, and the second set of transverse optical junctions 40g-l corresponds to a second layer of transverse optical junctions 40. The first and second layers of transverse optical junctions 40 are vertically offset from each other along the housing's height. Thus, optical signal propagation paths or optical axes corresponding to the first set of transverse optical junctions 40a-f (associated with the first layer of transverse optical junctions 40) can be positioned at least substantially parallel to a first transverse plane through the housing 20; and optical signal propagation paths or optical axes corresponding to the second set of transverse optical junctions 40g-l (associated with the second layer of transverse optical junctions 40) can be positioned at least substantially parallel to a second transverse plane through the housing 20.

In view of the foregoing, a flowcell embodiment such as that shown in FIGS. 1A-1F can accommodate up to six source optical signal modules 100a-f in a single layer configuration of transverse optical junctions 40; and up to twelve source optical signal modules 100*a-l* in a double layer configuration of transverse optical junctions. Other embodiments can include additional layers of transverse optical junctions 40. For purpose of simplicity and to aid understanding, portions of the description hereafter describe an embodiment that includes up to six transverse optical junctions 40*a-f* and at least one transverse optical junction layer. One of ordinary skill in the relevant art will readily understand that other embodiments can include other numbers of transverse optical junctions 40, where such embodiments can include identical or different numbers of transverse optical junctions 40 from one transverse optical junction layer to another.

Figure 2:
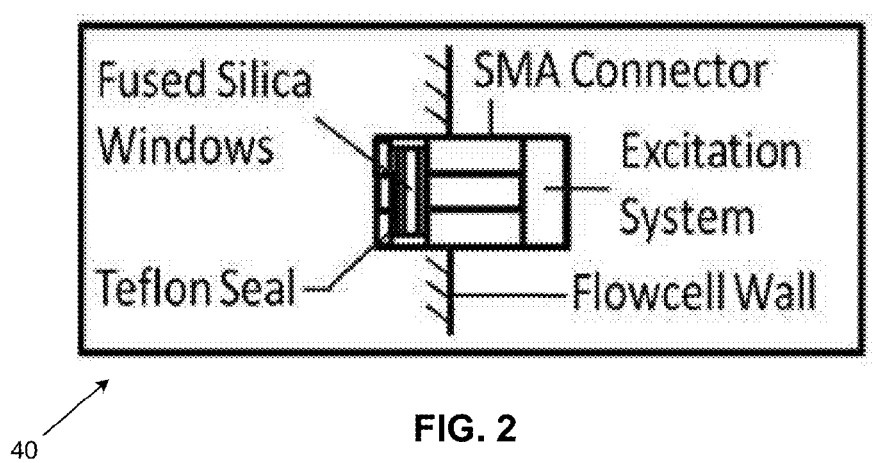
FIG. 2 is a side schematic illustration of a transverse optical junction in accordance with a representative embodiment of the present disclosure.

Referring also now to FIG. 2, a side schematic illustration of a transverse optical junction 40 in accordance with a representative embodiment of the present disclosure is shown. In a number of embodiments, each transverse optical junction 40 includes an optical window that is at least substantially transmissive with respect to an optical wavelength or wavelength range under consideration (e.g., a UV transmissive window), and which is resistant to chemical, thermal, and/or corrosive degradation. An optical window can include or be, for instance, a fused silica window. Each transverse optical junction 40 also includes at least one sealing element such as a Viton or Teflon O-ring to facilitate leak-resistant or leak-proof sealing relative to the internal channel 22. Each transverse optical junction 40 further includes a portion (e.g., female portion) of optical coupler or connector assembly such as a SubMiniature version A (SMA) type optical connector, which facilitates or enables coupling of the transverse optical junction 40 to an optical signal module 100.

Various embodiments of the flowcell 10 additionally include a lens assembly or lens 30 internally exposed to or disposed within the housing's internal channel 22, between the transverse optical junctions 40*a-f* and a central region or portion of the channel 22. The lens 30 is configured to facilitate or enable focusing of optical signals or beams provided by the source optical signal modules 100*a-f* to a spectroscopy measurement region within the channel 22, such as a central or centermost location, site, or point within the channel 22 (e.g., a multi-beam optical signal convergence position at an approximate transverse midpoint of the channel 22). In multiple embodiments, the lens 30 can include or be a plano-convex lens (e.g., a 6 mm plano-convex lens having a focal length of 10 mm), which is carried by or mounted upon a lens holder (e.g., a 13 mm lens holder, which can include a set of retaining or fastening elements, such as a pair of M1.6 screws). In several embodiments, the lens 30 is removable or replaceable, such that the lens 30 can be readily matched to the optical properties of a set of optical signal detection elements 300 (e.g., a set of optical fibers). The lens 30 and a corresponding lens holder can include or be fabricated from a material that is resistant to chemical, thermal, and/or corrosive degradation, in a manner analogous to that described above for the housing 20. As indicated in FIGS. 1A-1F, the flowcell 10 additionally includes at least one, and in multiple embodiments a plurality of (e.g., two) axial or longitudinal optical junctions 50*a,b*. Each axial optical junction 50*a,b* is configured for providing an optical signal propagation path and/or an optical axis that is substantially parallel to the length of the housing's internal channel 22. Each axial optical junction 50*a,b* can have a structure that is identical, essentially identical, analogous, or similar to that of a transverse optical junction 40*a-f*, in a manner readily understood by one of ordinary skill in the relevant art. An individual of ordinary skill in the art will also understand that in certain embodiments, an additional lens can be disposed between a given transverse optical junction 50*a,b* and a central or longitudinal axis corresponding to the flowcell's internal chamber 22, in a manner analogous or similar to that described above.

In some embodiments, a first axial optical junction 50*a* can facilitate or enable the delivery of optical signals from an additional source optical signal module 100*g* along a longitudinal or axial portion of the channel 22 within a central channel region. The first axial optical junction 50*a* can include or be coupled to one or more types of optical couplings, fittings, connectors, or signal transfer elements. A second axial optical junction 50*b* can facilitate or enable the detection or reception of optical signals that travel from the channel's central region to the second axial optical junction 50*b*, and the transfer of such detected or received optical signals to an optical signal detector, sensor, or characterization device (e.g., a spectrometer). An optical axis corresponding to the second axial optical junction 50*b* can be defined as an optical signal or emission reception, detection, or collection axis of the flowcell 10.

In other embodiments, each of the first and second axial optical junctions 50*a,b* facilitate or enable the detection or reception of optical signals that travel from the channel's central region to the first and second axial optical junctions 50*a,b*, respectively. In such embodiments, the detection of optical signals corresponding to the first and second axial optical junctions 50*a,b* can be facilitated or enabled by way of a bifurcated bundled optical fiber, where a first end of a read leg optically couples to the first axial optical junction 50*a*, and a second end of a read leg optically couples to the second axial optical junction 50*b*. The bundled optical fiber can be optically coupled, for instance, to a single optical detector.

Aspects of Representative Source Optical Signal Modules

Source optical signal modules 100 in accordance with various embodiments of the disclosure can be configured for providing, generating, outputting, and/or delivering optical signals appropriate for fluorescence spectroscopy, absorption spectroscopy, and/or turbidity measurements. Depending upon embodiment details, a source optical signal module 100 can carry or be optically coupled to a narrow band optical signal source, such as a set of single-color/single center wavelength or multi-color/multi-center-wavelength LEDs (e.g., a single LED or multiple LEDs) or a set of laser devices (e.g., a single semiconductor laser or multiple semiconductor lasers); or a multi-wavelength or broadband optical signal source (e.g., an optically enhanced broadband wavelength source such as a Heraeus Noblelight UV-VIS-DTM 6/10 S, 185-1100 nm light source). A source optical signal module 100 that carries or is coupled to a set of LEDs and/or a set of lasers can be well suited for facilitating fluorescence spectroscopy measurements (e.g., corresponding to LED Induced Fluorescence (LEDIF) measurements). A source optical signal module 100 that carries or is coupled to a multi-wavelength or broadband optical signal source can be well suited for facilitating absorption spectroscopy measurements.

In multiple embodiments, particular source optical signal modules 100 can be selectively or flexibly optically adjustable or tunable in one or more manners, as further described below. Source optical signal modules 100 in accordance with embodiments of the present disclosure can be utilized with optical flowcells 10 in accordance with embodiments of the present disclosure, or utilized in other or different types of flowcell designs and/or other or different types of optical measurement systems.

In an embodiment, an optical signal module 100 includes one or more optical signal generation elements such as an LED and/or a semiconductor laser that are carried internal to a housing, casing, or tube (e.g., at least one lens tube) having a length and a cross-sectional area or diameter. In a number of embodiments, the tube has an internal or inner diameter that is on the order of a cross-sectional area or diameter (e.g., an outer diameter) of an LED or laser device carried thereby. For instance, the tube can have an inner diameter that is less than 5×, less than 3×, between 1.25×-5×, or between 2×-3×, of the outer diameter of an LED package or a semiconductor laser package.

The optical signal module 100 can further include a number of optical path length tuning elements, which can include, for instance (a) lens elements and corresponding lens element carriers, retainers, or holders; (b) a number of spacing elements spacers disposable at one or more positions internal to the tube along the tube's length; and/or other types of elements. Elements of an optical signal module 100 can be rigidly instrumented (e.g., in a set of lens tubes) in a manner that facilitates or enables accurate and robust optical alignment, and which reduces or minimizes susceptibility to disturbances that may be encountered by an in-situ sensor. Representative implementations of particular types of source optical signal modules 100 are provided hereafter.

FIGS. 3A-3F are schematic illustrations of representative implementations of particular types of source optical signal modules 100 according to embodiments of the present disclosure. The representative implementations shown in FIGS. 3D-3G indicate particular part numbers corresponding to a Thorlabs optical systems catalog (Thorlabs, Newton, N.J. USA; www.thorlabs.com, www.thoriabs.hk).

Figure 3A:
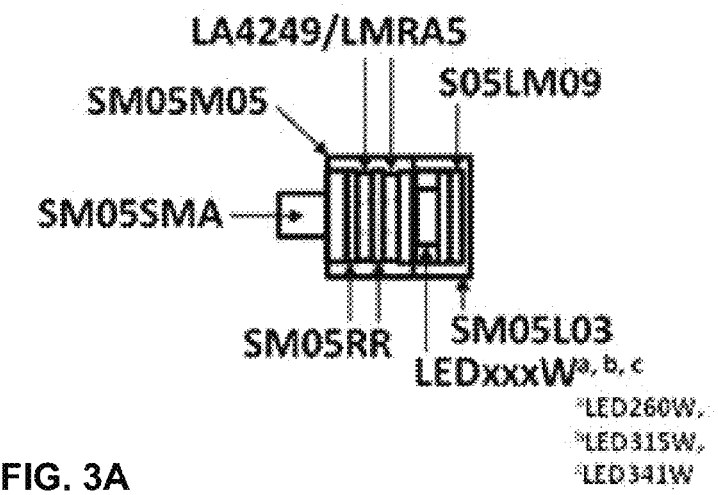
FIGS. 3A and 3B are schematic illustrations of a representative implementation of a source optical signal module corresponding to standard and extended optical path lengths respectively, for a first type of optical signal source in accordance with an embodiment of the present disclosure.
Figure 3B:
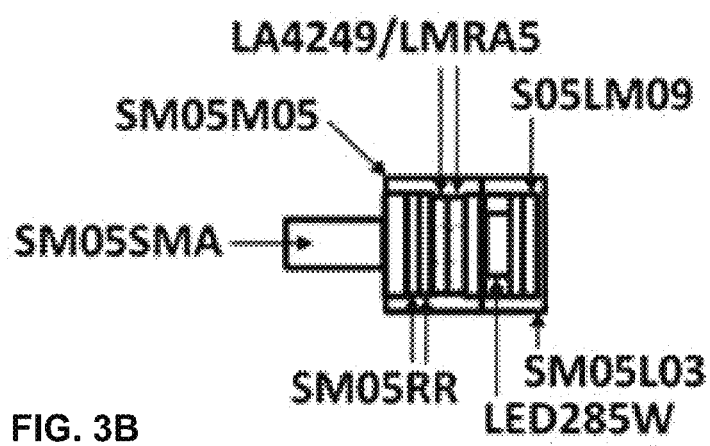

FIGS. 3A and 3B are schematic illustrations of a representative implementation of a source optical signal module corresponding to standard and extended optical path lengths respectively, for a first type of optical signal source (e.g., a TO-39 LED package) in accordance with an embodiment of the present disclosure. Particular implementation details corresponding to FIGS. 3A and 3B are as provided hereafter.

For deep UV LEDs having wavelengths ranging from 260 to 341 nm, the gap semiconductor is encased in a TO-39 package with a UV glass window. Commercially available UV LEDs from Thorlabs have HVA (half viewing angle) of 120 degrees. For this package, two plano-convex (compound) lenses of 5 (or 6 mm) in diameter, each of 10 mm in focal length mounted on a 13 mm (diameter) lens holder, are used to collect and then refocus the LED light from the semiconductor gap to the center of the flowcell, where fluorescence emission can be collected by a detector fiber instrumented perpendicular to the optical path of the LED excitation. The two lenses are separated by adjustable retaining rings, where the separation between the two lenses can be adjusted and thus the focal length of the compound lens can be established. Thus, the same design can be utilized to accommodate additional or other flowcell geometries. The beam produced exhibits a wide angle, similar to a circular scattering source where intensity rapidly decreases away from the semiconductor gap. As such, a UV glass window can be brought very close to or into contact with the first lens element, to optimize the collection of LED light from the source. For flowcell geometries in accordance with embodiments of the present disclosure, two optical layouts, namely, a standard optical pathlength geometry and an extended optical pathlength geometry, have been developed.

Standard optical path length geometry—for optically coupling LEDs such as Thorlabs LED260W, LED315W, and LED341W to a flowcell arrangement 10 such as that described above, the semiconductor gap should be focused at about 22.15 mm from the second lens element, which can be achieved by (i) placing the compound lens system 3 mm before the LED; (ii) separating the two singlets of the compound lens by 1.7 mm (e.g., using a single retaining ring); and (iii) separating the second singlets with the SMA connector (10 mm in length) adapter plate by 1.7 mm (a single retaining ring).

Extended optical pathlength geometry—for optically coupling an LED such as LED285W to a flowcell arrangement 10 such as that described above, the semiconductor gap should be focused at about 29.85 mm from the second lens element, which can be achieved by (i) placing the compound lens system 3 mm before the LED; (ii) avoiding separation between the two singlets; and (iii) separating the second singlets with the SMA (SMA 16 mm in length) connector adapter plate by 3.4 mm (using two retaining rings)

Such an optical arrangement 'virtually' shifts the gap semiconductor (excitation source) of the LED to the location where fluorescence emission is to be collected, hence, offering the optimum throughput for inducing fluorescence but at the same time fulfilling the optical cropping constraint placed by 2 mm fused silica windows of the flowcell 10. This can be qualitatively visualized by placing a piece of paper that can fluoresce in the presence of the excitation light at the geometrical center (where all six excitation light meets) of the flowcell liquid channel or chamber 22. The virtual image of the gap semiconductor of the LED can be observed to focus at (or very close to) the center of flowcell's internal channel 22.

FIGS. 3C and 3D are schematic illustrations of a representative implementation of a source optical signal module configured for providing a wide half view angle and a narrow half view angle, respectively, for a second type of optical signal source (e.g., an InGaN type LED) in accordance with an embodiment of the present disclosure. Particular implementation details corresponding to FIGS. 3C and 3D are as provided hereafter.

Tunable throughput optimizer for InGaN type LED: the near UV to visible LEDs include heterostructures grown on an InGaN substrate. The diode is encapsulated in a round clear epoxy casing with a 5 mm diameter for different HVA LEDs. For this package, two plano-convex lenses of 12.7 mm in diameter, each having a 20 mm focal length, are used to collect and then refocus the LED light from the semiconductor gap to the center of the flowcell 10, where fluorescence emission is to be collected by a detector fiber instrumented perpendicular to the optical path of the LED excitation. The InGaN type LED has an epoxied hemisphere before the LED that serves as a ball lens to focus the light to a certain degree; hence, the beam is of a (much) narrower angle when compared to a deep UV LED (such as a ZnO/AlGaN/GaN/InN type LED in a TO-39 package). For the flowcell geometry, two optical layouts, namely, a wide half view angle layout and a narrow half view angle layout, have been developed.

Wide half view angle layout—for coupling an LED such as Thorlabs LED370E (HVA 19 degrees) with a flowcell arrangement 10 such as that described above, the semiconductor gap should be focused at about 26.45 mm from the second lens element, which can be achieved by (i) Placing the compound lens system at 8.5 mm (equivalent to five Thorlabs SM05RR retaining rings) from the base of the LED; (ii) separating the two singlets by 6 mm (readily achievable by putting five Thorlabs SM05RR retaining rings between the two singlets; and (iii) avoiding separation between the second singlet and the SMA (16 mm in length) connector adapter plate. This optical layout 'virtually' shifts the gap semiconductor (excitation source) of the LED to the location where fluorescence emission is to be collected, and at the same time fulfills the optical cropping constraint placed by a 2 mm fused silica windows of the flowcell 10. This can be qualitatively visualized by placing a piece of paper that can fluoresce in the presence of the excitation light at the geometrical center (where six excitation optical paths meet) of the flowcell internal channel or chamber 22. The virtual image of the gap semiconductor of the LED can be observed to focus at (or very close to) the center of the flowcell 10.

Narrow half view angle layout—for coupling an LED such as Thorlabs LED405E (HVA 5 degrees) with a flowcell arrangement 10 such as that previously described, the semiconductor gap should be focused at about 26.45 mm from the second lens element, which can be achieved by (i) placing the compound lens system at ~22.8 mm from the base of the LED; (ii) avoiding separation between the two singlets, thus, creating a custom equivalent BFL of ~10 mm that is not commercially available for singlet of 12.7 mm in diameter; and (iii) avoiding separation between the second singlets with the SMA (16 mm in length) connector adapter plate.

Figure 3E:
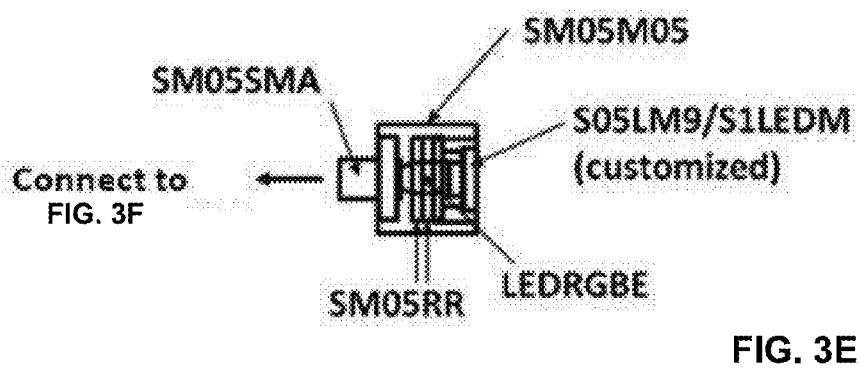
FIGS. 3E and 3F are schematic illustrations of a representative implementation of a holder and an optical path corrector, respectively, corresponding to thirdd type of optical signal source in accordance with an embodiment of the present disclosure.
Figure 3F:
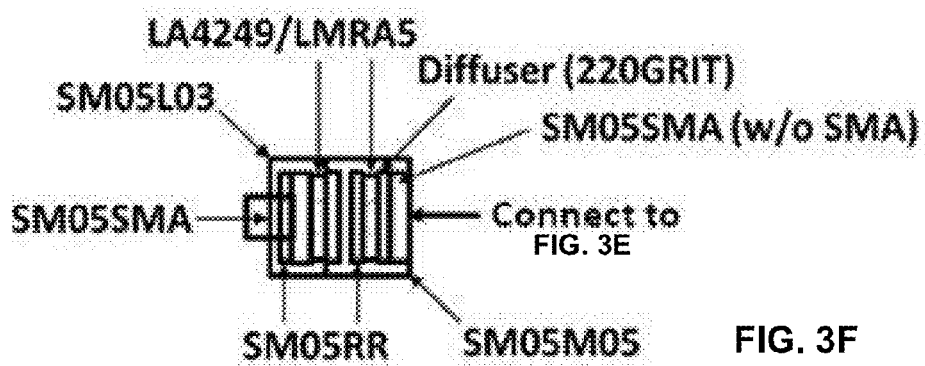

FIGS. 3E and 3F are schematic illustrations of a representative implementation of a holder and an optical path corrector, respectively, corresponding to third type of optical signal source (e.g., an InGaN type tri-wavelength LED) in accordance with an embodiment of the present disclosure. Particular implementation details corresponding to FIGS. 3E and 3F are as provided hereafter.

Optical path corrector for InGaN type tri-wavelength LED: The tri-wavelength LED includes heterostructures grown on an InGaN substrate. The diode is encapsulated in a round clear epoxy casing with a 5 mm diameter. For this package, a custom holder is designed to hold the LED in place, where the tip of the LED is put in contact with the SMA (10 mm in length) of the connector adapter plate. An optical path corrector is attached before the SMA of the custom holder. The optical path corrector can include a diffuser (i.e., 220 GRIT) and two plano-convex lenses of 5 mm (or 6 mm) in diameter, each of 10 mm in focal length, to collect and then refocus the LED light to the same optical path in-line with the geometrical centerline of the LED. A custom circuit powerboard can be used to select or control the throughput of each individual optical wavelength.

Relative to absorption measurements, in addition or as an alternative to including optical pathlength adjustment or establishment elements (e.g., spacer elements), the intensity of the multi-wavelength excitation system for absorbance measurements can be varied with a potentiometer, thus effectively varying excitation intensity in a manner that can effectively serve the same purpose.

Aspects of Representative Optical Emission Collection Apparatuses or Systems

Figure 4A:
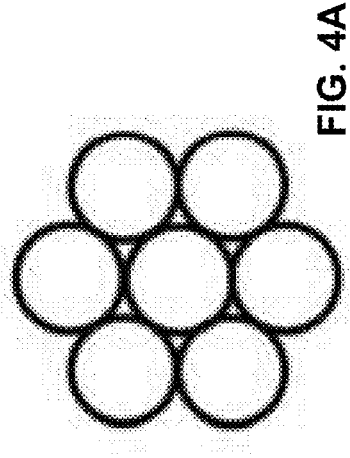
FIG. 4A is a schematic illustration of a set of bundled fibers forming portions of an optical emission collection apparatus, subsystem, or system in accordance with an embodiment of the present disclosure.
Figure 4B:
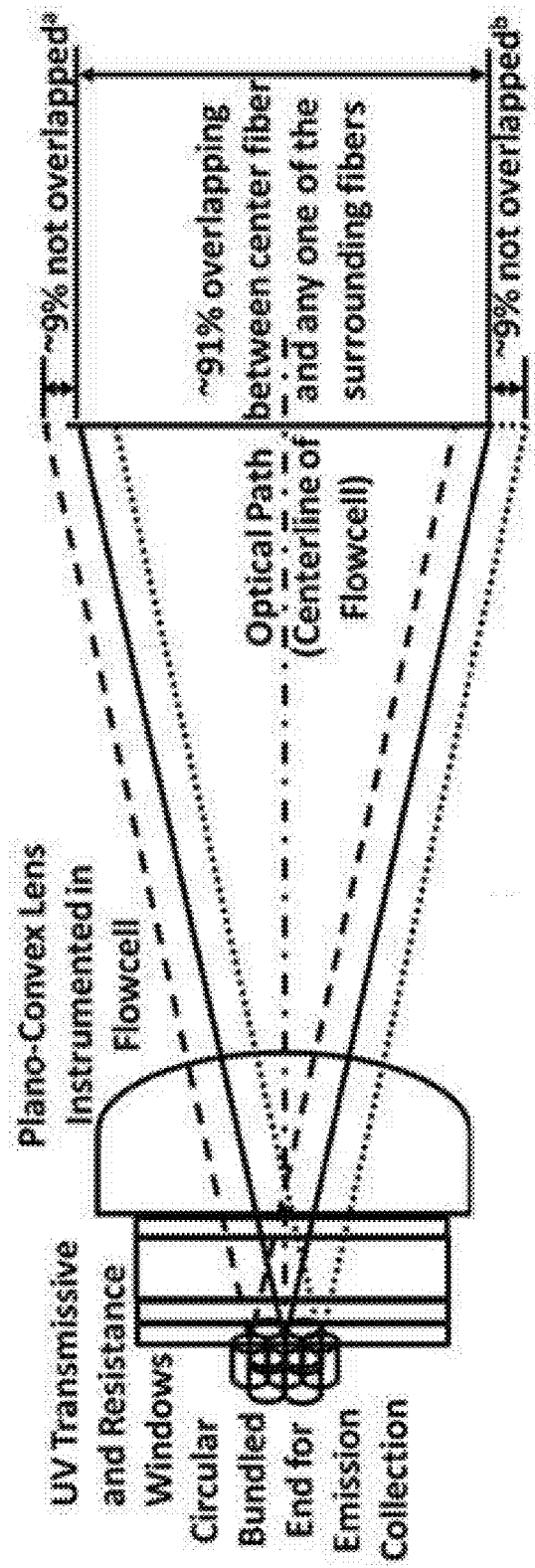
FIG. 4B is a schematic illustration of the set of bundled fibers disposed relative to portions of a flowcell axial optical junction in accordance with an embodiment of the present disclosure.
Figure 4C:
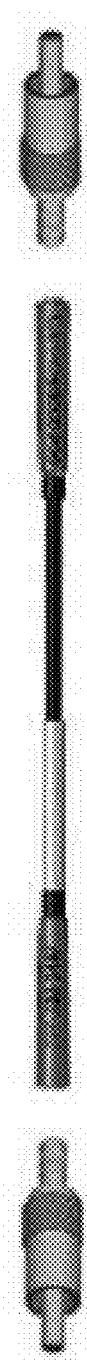
FIG. 4C is an illustration of a bundled fiber assembly in accordance with an embodiment of the present disclosure.
Figure 4D:
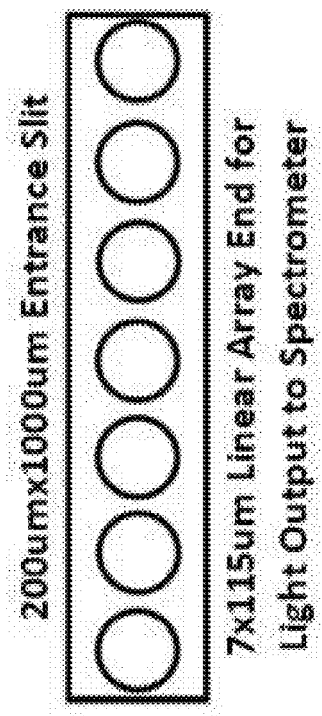
FIG. 4D is a schematic illustration of a representative spectrophotometer entrance slit structure in accordance with an embodiment of the present disclosure.

FIGS. 4A-4D are schematic illustrations of portions of an optical emission collection apparatus, subsystem, or system 200 in accordance with an embodiment of the present disclosure. More particularly, FIG. 4A is a schematic illustration of a set of bundled fibers; FIG. 4B is a schematic illustration of the set of bundled fibers disposed relative to portions of a flowcell axial optical junction; FIG. 4C is an illustration of a bundled fiber assembly in accordance with an embodiment of the present disclosure; and FIG. 4D is a schematic illustration of a representative spectrophotometer entrance slit structure in accordance with an embodiment of the present disclosure. Particular details corresponding to a representative implementation of such an optical emission collection system 200 are provided hereafter.

A 6 mm diameter plano-convex lens (convex surface is the wetting surface) of focal length 10 mm is disposed ~2 mm in front of a circular bundle to linear array patch fiber, which includes 7×115 um fiber cores. A circular bundle end is connected to an SMA optical junction (i.e., an axial optical junction 50b) of the flowcell 10, where a UV transmissive and degradation resistive window (such as fused silica) with O-ring type sealing (such as Viton or Teflon) separate the lens and the circular bundle end. The linear array end is connected to the SMA of a spectrometer instrumented with an entrance slit of 200 um (W)×1000 um (L). The circular bundle end and linear array end of the patch fiber can be keyed (e.g., notched) to ensure proper alignment for every reconnection of the patch fiber to the associated SMAs.

Each individual fiber core of N.A. 0.22 is observing a cone of light equivalent to a projected diameter of ~1.33 mm on the surface of the plano-convex lens (6 mm in diameter) and the overlapping in projected diameter between the center fiber and any one of the surrounding fibers at the surface of the lens is 91% (~82.7% in surface area), leading to a tremendous improvement of intensity per unit of observable area. This improvement is particularly effective with respect to flowcell geometry, where emission collection is highest corresponding to the center (optical path of emission collection) of the flowcell's internal channel 22. The total observable surface area by the circular bundle end corresponding to the surface of the internal lens is 1.56 mm (1.67 mm if fiber is not treated as a point source) in projected diameter, fulfilling the optical cropping constraint placed by the 2 mm fused silica windows of flowcell geometry and at the same time avoiding any optical aberration due to the 6 mm internal lens. The internal lens of the flowcell 10 collects emission at a distance corresponds to the focal length (f/10 mm) of the internal lens. The same design and utilities can be extended to other flowcell geometries, such as by changing the size and focal length of the lens.

The length of the linear array end configuration corresponds to the entrance slit height (or length) of the spectrometer in use with the sensor, delivering the optimum throughput in the vertical axis. The fiber core diameter can be selected such that the height (1050 um) of the stacked linear array closely matches the height of the spectrometer's entrance slit (1000 um). Additionally, each individual fiber core is configured for collecting emission at (or very close to) the center of the flowcell where the intensity per unit of observable area is highest. Since the fiber core is smaller than the slit width, it also effectively avoids any diameter edge light losses due to misalignment in patching.

Note that the specifications of a circular to linear array fiber such as that described herein can be selected to correspond with the flowcell geometry and a particular spectrometer employed in an LED-induced fluorescence sensor. For a spectrometer without an entrance slit, the resolution and throughput of the emission collection are dictated by the (linear array) fiber transmitting light into the spectrometer. If throughput collection is favored over resolution, which is generally accepted in spectrofluorometry due to broad emission spectrum profiles, the core of the individual fibers can be increased to 200 um. Alternatively, a 1000 um single core fiber can be used in place of a patch fiber. The fiber can be custom patched from a vendor such as Ocean Optics.

Aspects of Representative Deployment Platforms

A representative LEDIF sensor module, assembly, or system (hereafter referred to as a LEDIF sensor, LEDIF system, or simply LEDIF for purpose of simplicity and to aid understanding) in accordance with an embodiment of the present disclosure is described hereafter. A LEDIF sensor can be a low cost real-time multi-platform deployable module for in-situ sensing of water chemistry, which employs optical spectroscopic sensing techniques. The LEDIF sensor includes at least one multiple-optical-junction flowcell 10 such as that described above, which can be outfitted or instrumented with a number of source optical signal modules 100 as well as an optical signal reception/detection or emission collection apparatus, subsystem, or system 200. The source optical signal modules 100 can include low cost single- or multi-chip custom packaged light emitting diodes (LEDs) of different wavelengths, which are optically enhanced by a series of custom designed miniature tunable optical elements, structures, or devices as previously described to produce an optimized excitation-emission collection system configured for spectrofluorometry.

An optically enhanced broadband wavelength (such as Heraeus Noblelight UV-VIS-DTM 6/10 S, 185-1100 nm) light source coupled with a custom fiber-optical system can be instrumented directly opposite (e.g., axially or longitudinally opposite) to an emission collection system 200, enabling absorbance measurement within the same instrument. Turbidity is measured within the same flowcell 10 using the Nephelometry principle of sensing with the multi-wavelength LED optical system. Three measurement modalities (fluorescence, absorbance, and turbidity) are all observed with a spectrometer (such as an Ocean Optics USB4000 or STS spectrometer) and the data are processed and/or recorded by way of an instruction processing device such as a microprocessor, a microcontroller, or a computer, for instance, a single board computer (e.g., a Technologic Systems TS-7260). The computer can communicate with a remote or external computing system or device and/or a communication network by way of one or more communication interfaces (e.g., a USB interface, an SSH interface, an Ethernet interface, a wireless communication interface such as a mobile telephony or paging network interface, and/or another type of interface). The system can be powered with a 48V (110 Wh) battery that is DC-DC converted with a powerboard to distribute power to various onboard devices, apparatuses, subsystems, or equipment. Battery specifications can be selected for enabling power diversion to a host deployment platform (e.g., an AUV) in the event of an emergency situation or reaching a power depletion threshold. Other battery designs that match particular requirements of the powerboard can be used, whenever applicable. Custom or customizable software code or program instruction sets (e.g., executable by a processing unit), and associated computer-readable/electronically-readable media (e.g., one or more memories, which can correspond to fixed and/or removable data storage media) are provided for controlling onboard instruments and performing data collection/analysis operations.

Figure 5A:
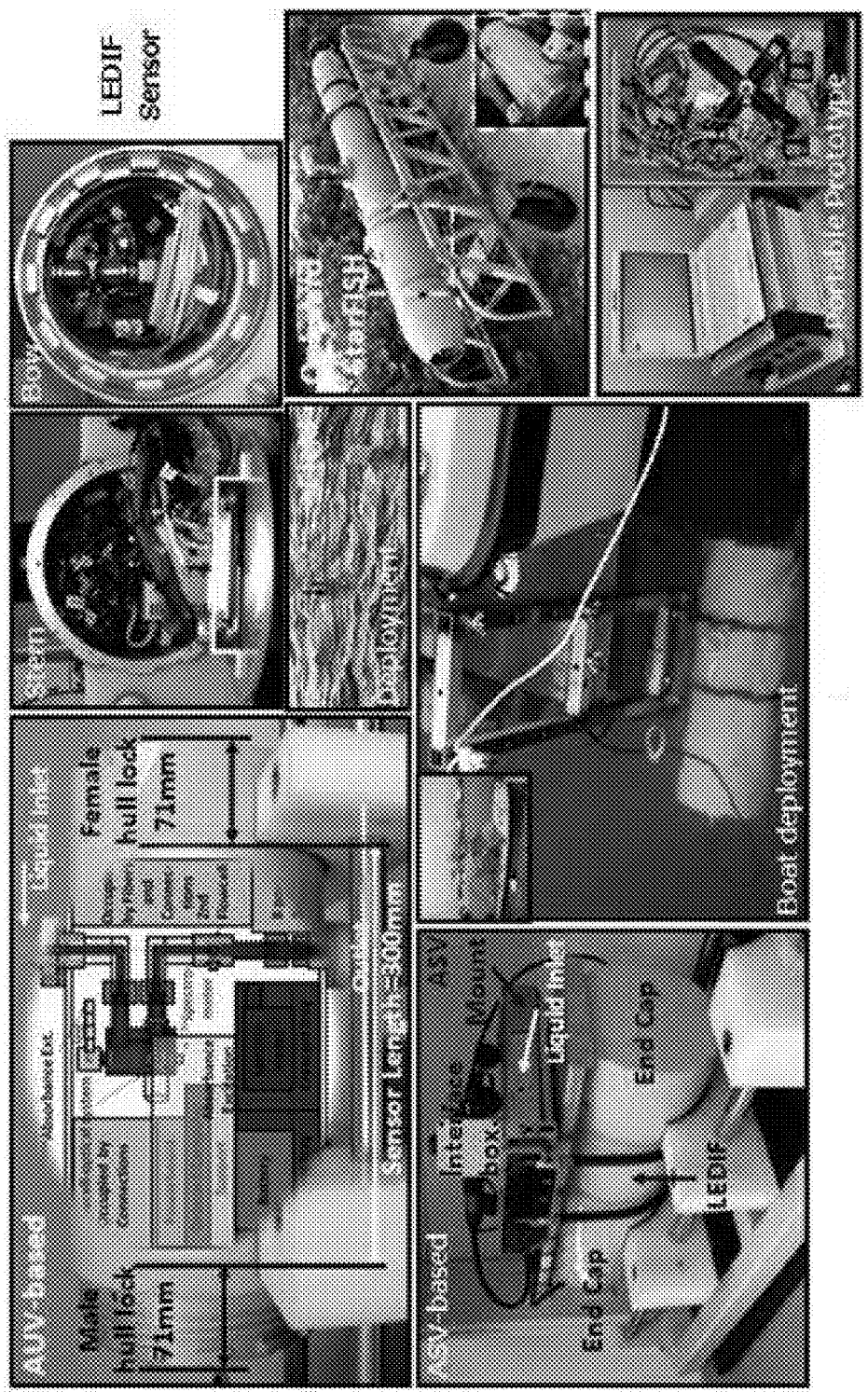
FIGS. 5A and 5B illustrate various representative types of platforms that can be configured for carrying (e.g., in an integral or internal manner) a LEDIF system in accordance with an embodiment of the present disclosure.
Figure 5B:
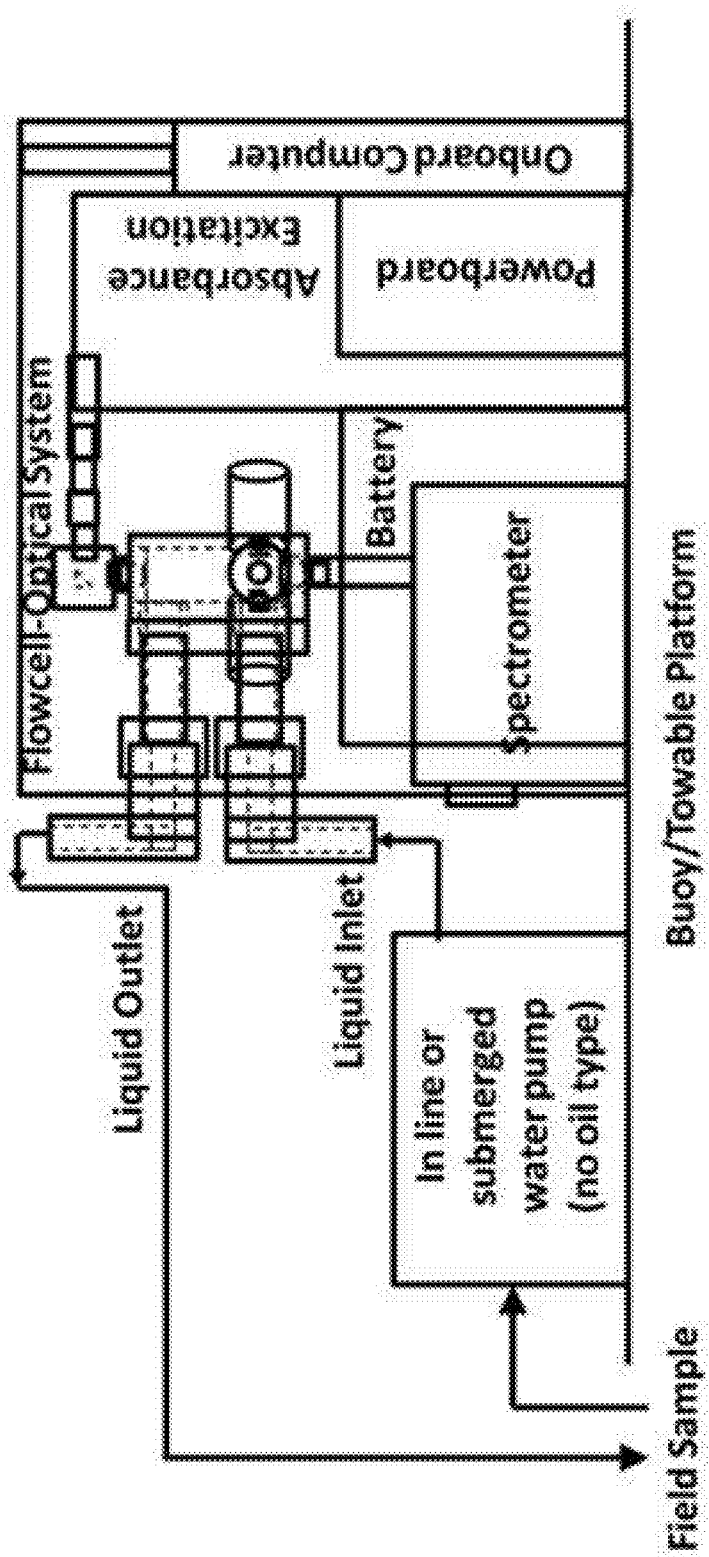

Capabilities and Function: The LEDIF is capable of recording in-situ real-time fluorescence, absorbance, and turbidity measurements within a single instrument. The multi-spectral capability rapidly provides multiple spectra containing information on water chemistry, where the data acquisition rate depends only on the integration time. The multi-wavelength excitation capabilities enable the recorded emission spectrum to be translated into an excitation-emission matrix spectrum, comparable to results obtainable by way of a broadband excitation lab-based fluorometer. Low power consumption (corresponding to the use of light emitting diodes as excitation sources and a unique flow feeding manifold without the use of a pump), low cost, favorable detection limits, ultra-compact packaging, with little or no maintenance make sensors or sensing systems in accordance with several embodiments of the present disclosure suitable for limnology and oceanography research, essentially bringing the lab to the water and overcoming many shortcomings of current technology. FIGS. 5A and 5B illustrate various representative types of platforms that can be configured for carrying (e.g., in an integral or internal manner) a LEDIF system in accordance with an embodiment of the present disclosure. FIG. 5B corresponds to a packaging structure (e.g., a housing or enclosure) for a PORTA/BUOY-LEDIF system having representative dimensions of 200 mm (L)×150 mm (W)×200 mm (H).

Figure 6A:
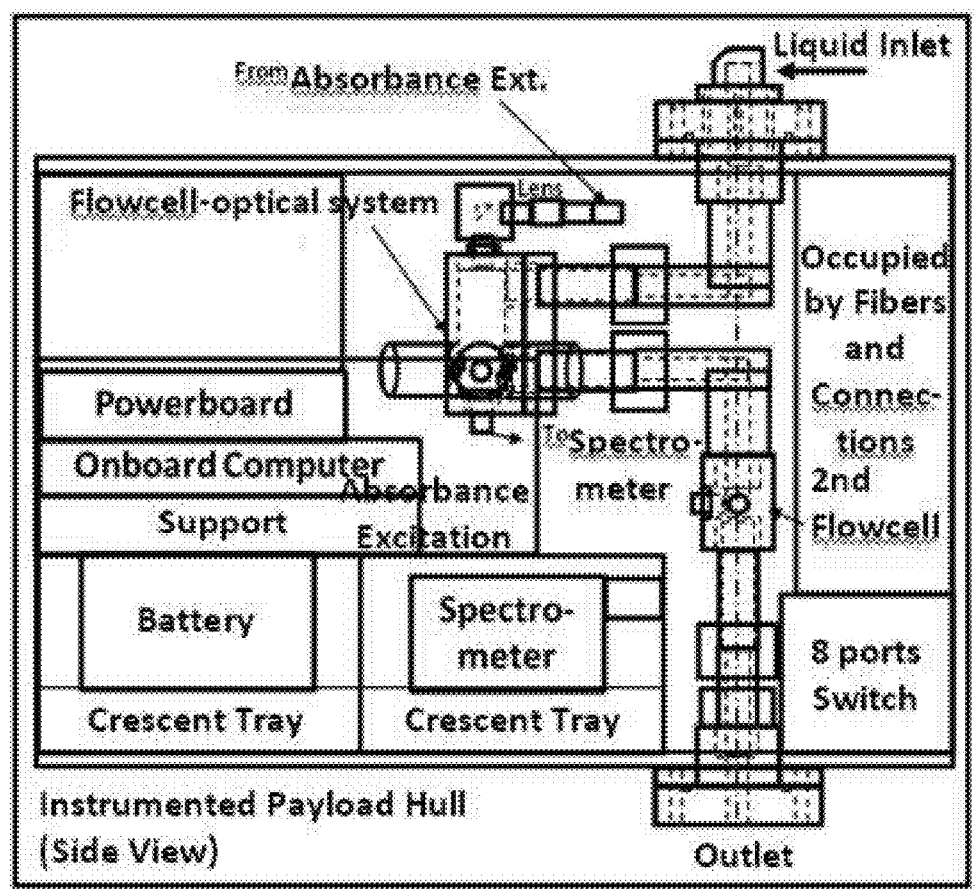
FIG. 6A is a schematic illustration of LEDIF sensor layout in accordance with an embodiment of the present disclosure.
Figure 6B:
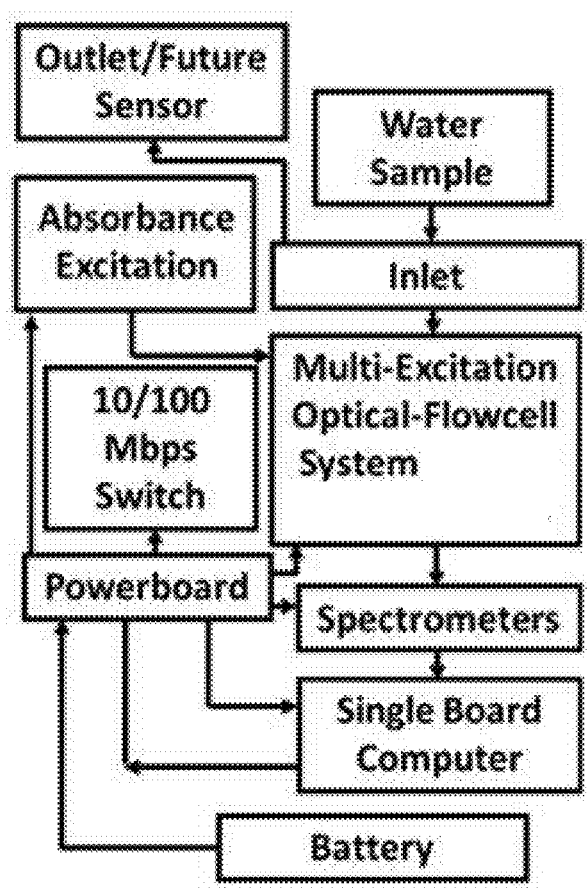
FIG. 6B is a block diagram of particular LEDIF elements and corresponding LEDIF operations or processes in accordance with an embodiment of the present disclosure.

Sensor Layout: The LEDIF includes (1) a flowcell; (2) a series of optical modules or systems; (3) a data logging system; (4) a powerboard and onboard computer; and (5) a battery, all of which are packaged within a highly compact 200 ($\phi$)×300 mm (L) cylindrical enclosure, e.g., which can be seamlessly integrated to a Small Team of Autonomous Robotic Fish (STARFish) AUV. FIG. 6A is a schematic illustration of LEDIF sensor layout, and FIG. 6B is a block diagram of particular LEDIF elements and corresponding LEDIF operations or processes in accordance with an embodiment of the present disclosure.

Figure 7:
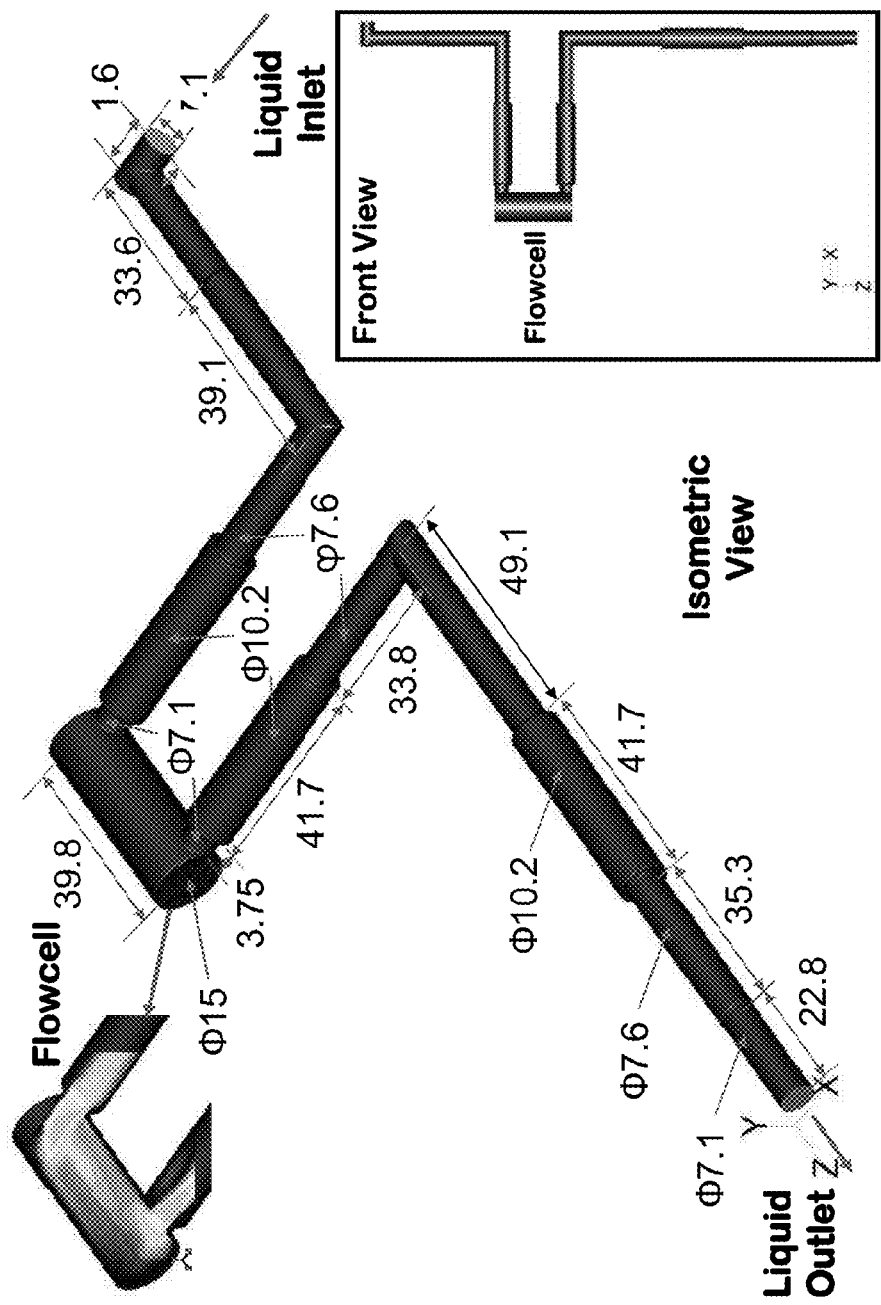
FIG. 7 shows a liquid chamber of a through-hull flow transportation manifold in accordance with a representative embodiment of the disclosure, where dimensions are indicated in mm.
Figure 8A:
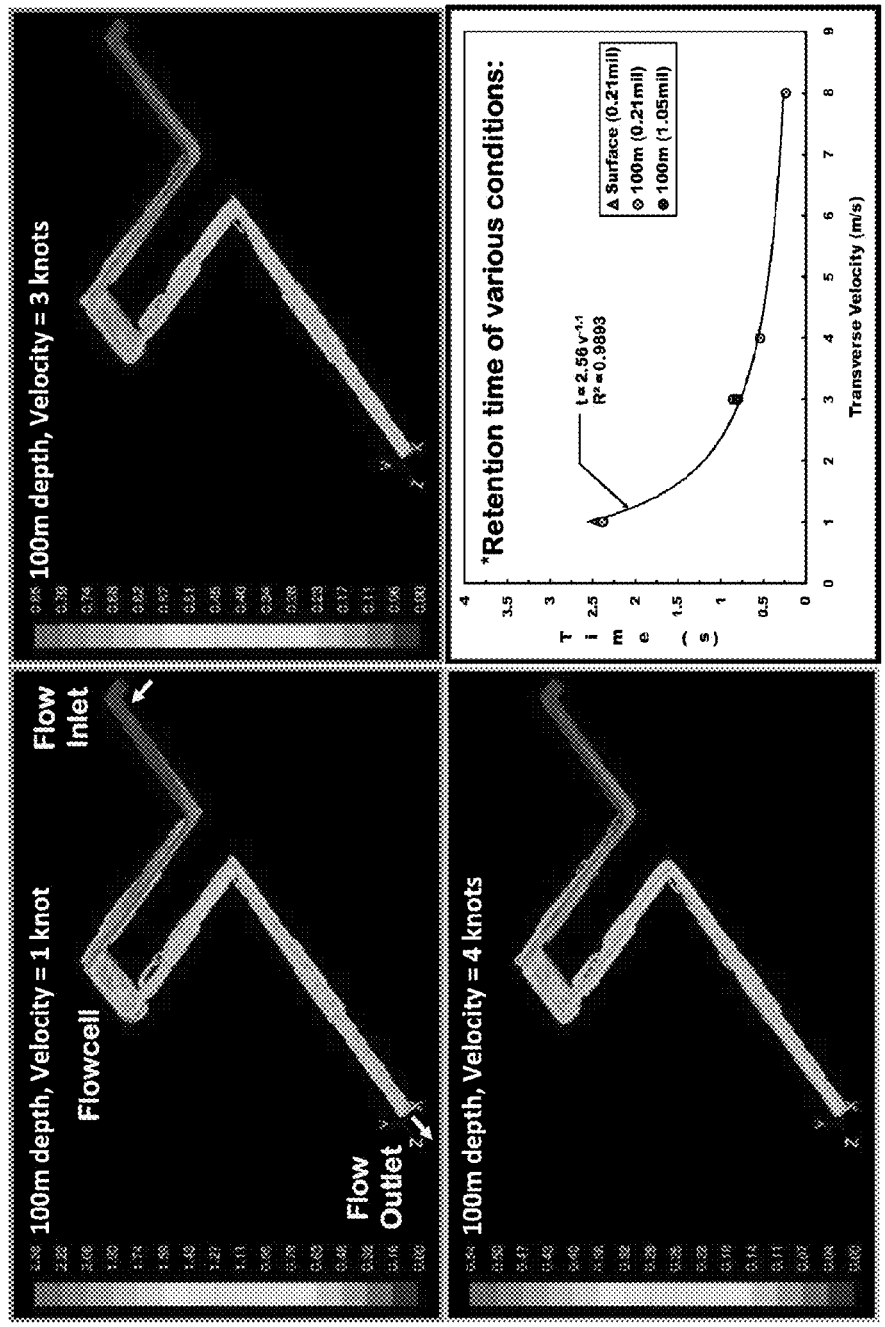
FIG. 8A illustrates sensing location and time extraction with respect to a host platform in accordance with an embodiment of the present disclosure.
Figure 8B:
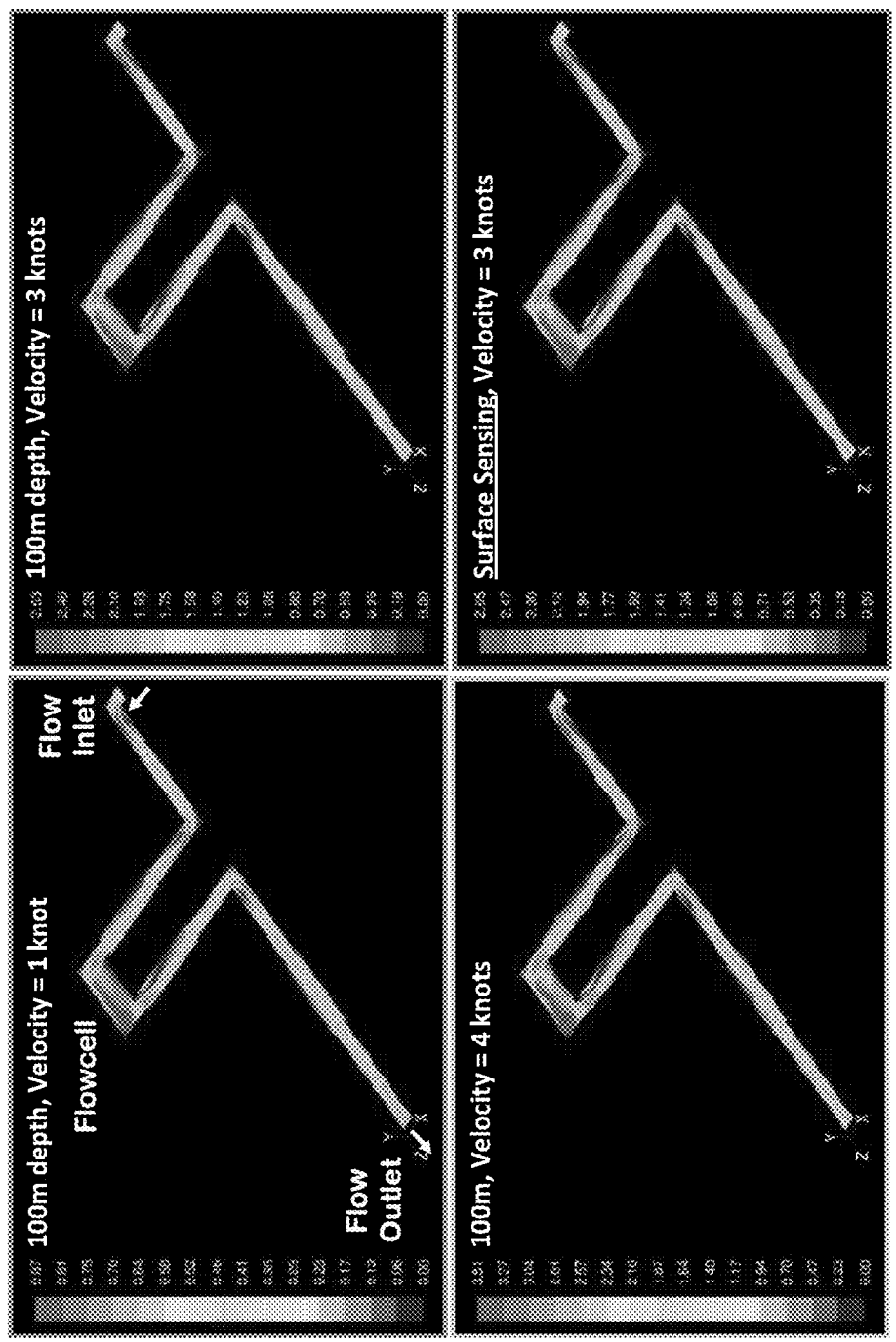
FIGS. 8B and 8C show a modeled internal flowfield (e.g., corresponding to a velocity contour) and an associated mesh density validation in accordance with an embodiment of the present disclosure.
Figure 8C:
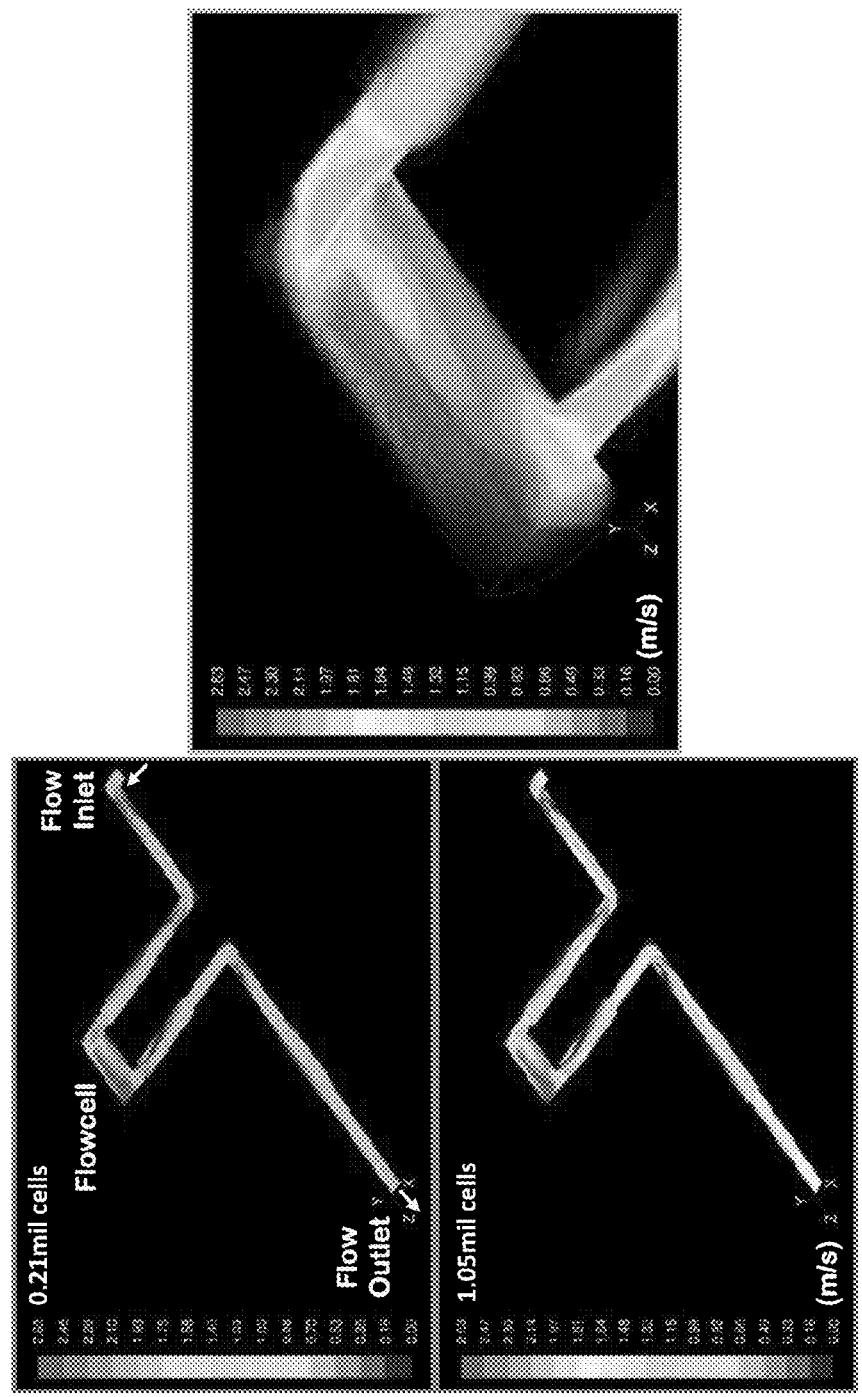

Flow Feeding: FIG. 7 shows a liquid chamber of a flow transportation manifold (e.g., a through hull manifold) in accordance with a representative embodiment of the disclosure, where dimensions are indicated in mm. As a LEDIF system transverses through the field, fresh sample is continuously fed into its flowcell 10 to replace the existing sample (pushed towards the exit) employing the uniquely designed through hull flow feeding manifold. An inlet of the flowcell 10 can be tapered (e.g., in accordance with a funnel shape) to facilitate or enhance fluid flow into the flowcell 10. The transverse velocity of the sensor module can be automatically synchronized to the rate of flow feeding, with the retention time/delay time associated with the transverse speed described in FIG. 8A, allowing the location and time of sensing to be easily extracted with respect to the host platform. FIGS. 8B and 8C show a modeled internal flowfield of the flowcell (e.g., corresponding to a velocity contour (m/s)) and an associated mesh density validation, for modeled conditions corresponding to 100 m depth, and 3 knots. The simple yet effective design is particularly suitable for an autonomous vehicle platform as it does not require the use of a pump, thus favoring compact packaging and reducing power consumption.

Flowcell: A highly compact (dimension ~37 mm (W)×61 mm (L)) multi-optical junction optical flowcell 10 permits the concurrent instrumentation of multi-excitation optical systems for fluorescence, absorbance, and turbidity measurements within the same flowcell 10. The flowcell 10 is instrumented out-of-line with respect to the liquid inlet and outlet to the enclosure; with liquid entering and exiting the flowcell 10 from the sides, effectively preventing stray light from entering the flowcell 10, thus simplifying background removal during sensing.

Excitation-Emission Optical System: A series of ultra-compact (dimension ~12.7 ($\phi$)×25.4-50.8 mm (L)) optical modules, apparatuses, or systems capable of optimizing the throughput of commercially available low cost LEDs corresponding to one or more package types (such as TO-39 and HS (heterostructures) on InGaN substrate) for inducing fluorescence, and the coupling of a collective lens with a bundle array patch (or a single core) fiber for the collection of emission spectrum have been developed.

Figure 9:
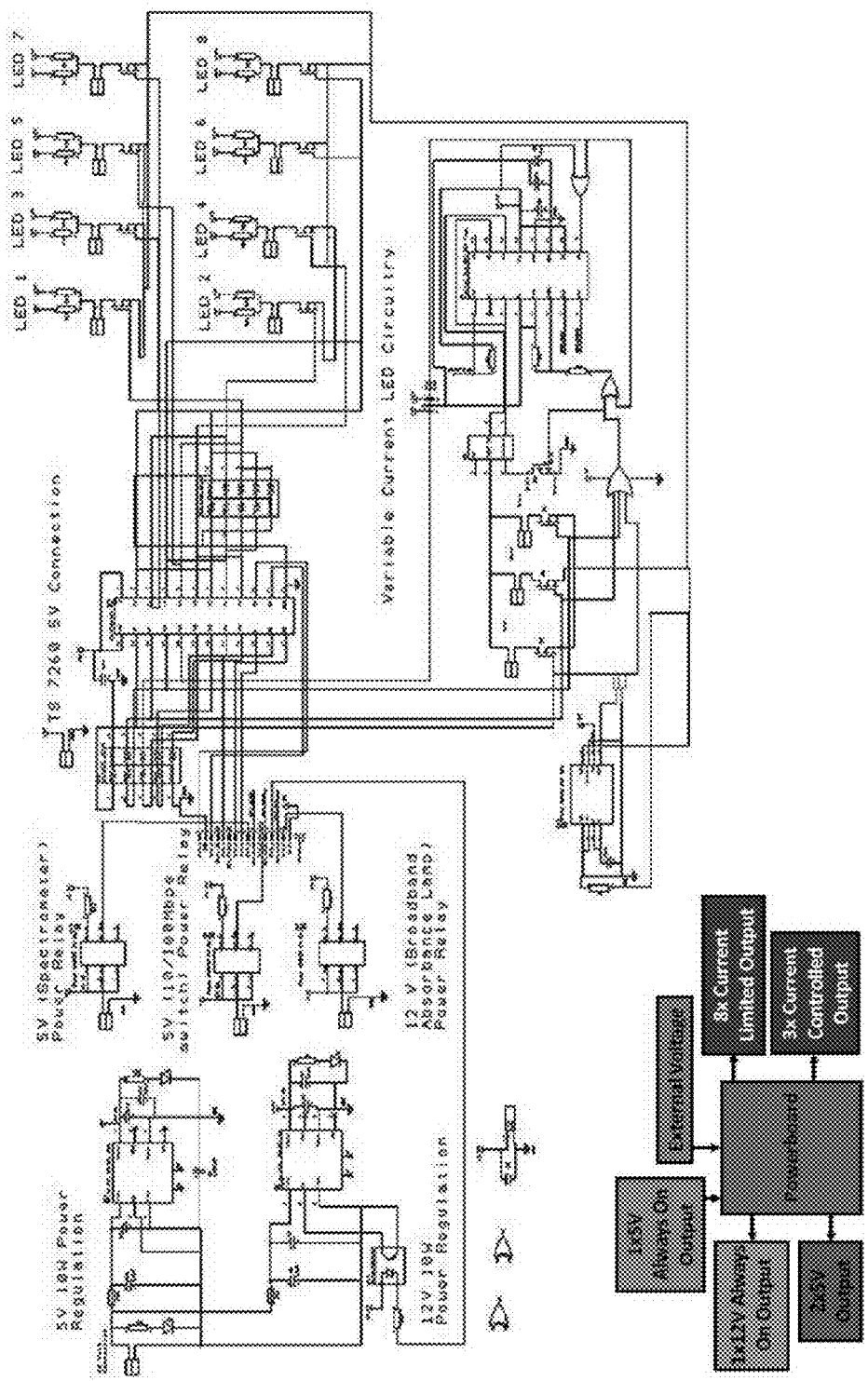
FIG. 9 is a circuit diagram of a LEDIF powerboard in accordance with an embodiment of the present disclosure.

Powerboard: FIG. 9 is a circuit diagram of a LEDIF powerboard in accordance with an embodiment of the present disclosure. The LEDIF powerboard can be a generic power management and control system for low power in-situ sensing platforms. It can power various loads at 5 or 12 volts, with the capability of implementing programmable control on various types of loads for limiting unnecessary power draw. In essence, the LEDIF powerboard provides the following functionality and/or performs the following functions: (1) DC-DC conversion of external 20 to 70 volts (such as from a battery) down to 5 volts; (2) programmatic control of DC-DC conversion of external 20- to 70 volts down to 12 volts; (3) one connection to 5 volts which is always on when the board is powered; (4) two programmatically controlled independent connections to 5 volts at 2.5 A; (5) one programmably controlled connection to 12 volts at 2.5 A; (6) eight current limited, programmably controlled outputs at user selectable 5 volts or 12 volts rated up to 100 mA; and (7) three programmable current outputs at 5 volts rated up to 20 mA. The programmably controlled 5 volt and 12 volt connections can be used to power external devices such as spectrometer, broadband absorbance lamp, pump, or 10/100 Mbps switch, among others. The eight current limited outputs and the three programmable current outputs can be used to power LEDs or other constant current devices.

Software: A software platform (known as iLEDLIF), written in C++ using standard C/C++ libraries, was developed to handle asynchronous communication between various sensors and actuators via an embedded computer system that runs on the Debian Linux operating system. FIG. 10 shows a iLEDLIF source code process in accordance with a representative embodiment of the present disclosure. iLEDLIF handles communication with external devices by way of serial, USB, RJ-45, digital input/output, and/or other interfaces or connections as well as communication with virtual devices implemented entirely in the software; and is fully configurable on launch via an EML configuration file. iLEDLIF acts as a message carrier between each real and virtual device loaded at program launch. Each message specifies (1) a message source device; (2) a message destination device; and (3) information to be conveyed by the message. Each device implements within its driver one or more manners of processing or responding to a specific message. Any device can attempt to send any message to any other device. Messages are delivered on a first-in-first-out basis and are queued within the device driver. The device driver handles each message on a first-in-first-out basis.

The operations of an iLEDLIF can include the following: (1) receive or read in configuration details from an XML configuration file; (2) load device drivers for literal and virtual devices; (3) wait for communication to be initiated from any of the literal or virtual devices, such that (a) if a message is received, send the message to a message destination device driver; and (b) the message destination device driver performs an appropriate action depending on the message received. In various embodiments, the iLEDLIF software platform includes a built in scripting language that provides a software user interface which enables users to generate text files specifying a series of commands, without needing to write, compile, or understand conventional programming language (e.g., C++) code. A representative example of a user generated program or script, written in accordance with a scripting language, is shown in FIG. 11. The execution of such a script will result in looping through 6 LED wavelengths to perform emission spectrum measurements, followed by repeating this loop twice. A reference scan of the background is also obtained.

Data Logger: The emission spectrum can be recorded with a spectrometer (such as an Ocean Optics Model USB4000 or STS) and, in an AUV or similar type of application, the data can be stored or relayed to a chase boat via an AUV MCU using an onboard computer (e.g., a Technologic System Model TS-7260).

Figure 12A:
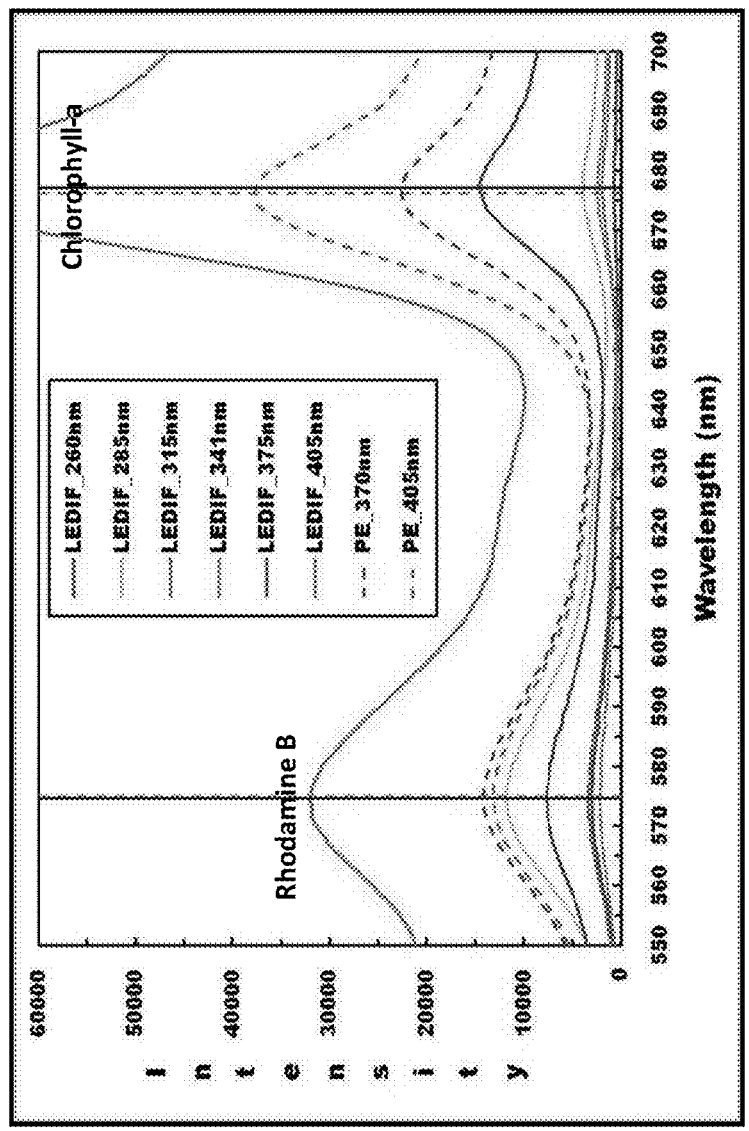
FIG. 12A shows a comparison of fluorescence peaks of a lab mixture between a LEDIF sensor in accordance with an embodiment of the present disclosure and a typical high-end lab-based fluorometer such as a Perkin Elmer LS55.

Assessments: FIG. 12A shows a comparison of fluorescence peaks of a lab mixture between an LEDIF sensor in accordance with an embodiment of the present disclosure and a typical high-end lab-based fluorometer such as a Perkin Elmer LS55. Owing to difference in counts to photon ratio, the intensity of the Perkin Elmer LS55 fluorometer is multiplied by a correction factor of ~63.5, effectively increasing the intensity to the same order measured with LEDIF. The observed peaks of the two sensors have a percent difference of 0.07% and 0.12%, showing excellent agreement.

Figure 12B:
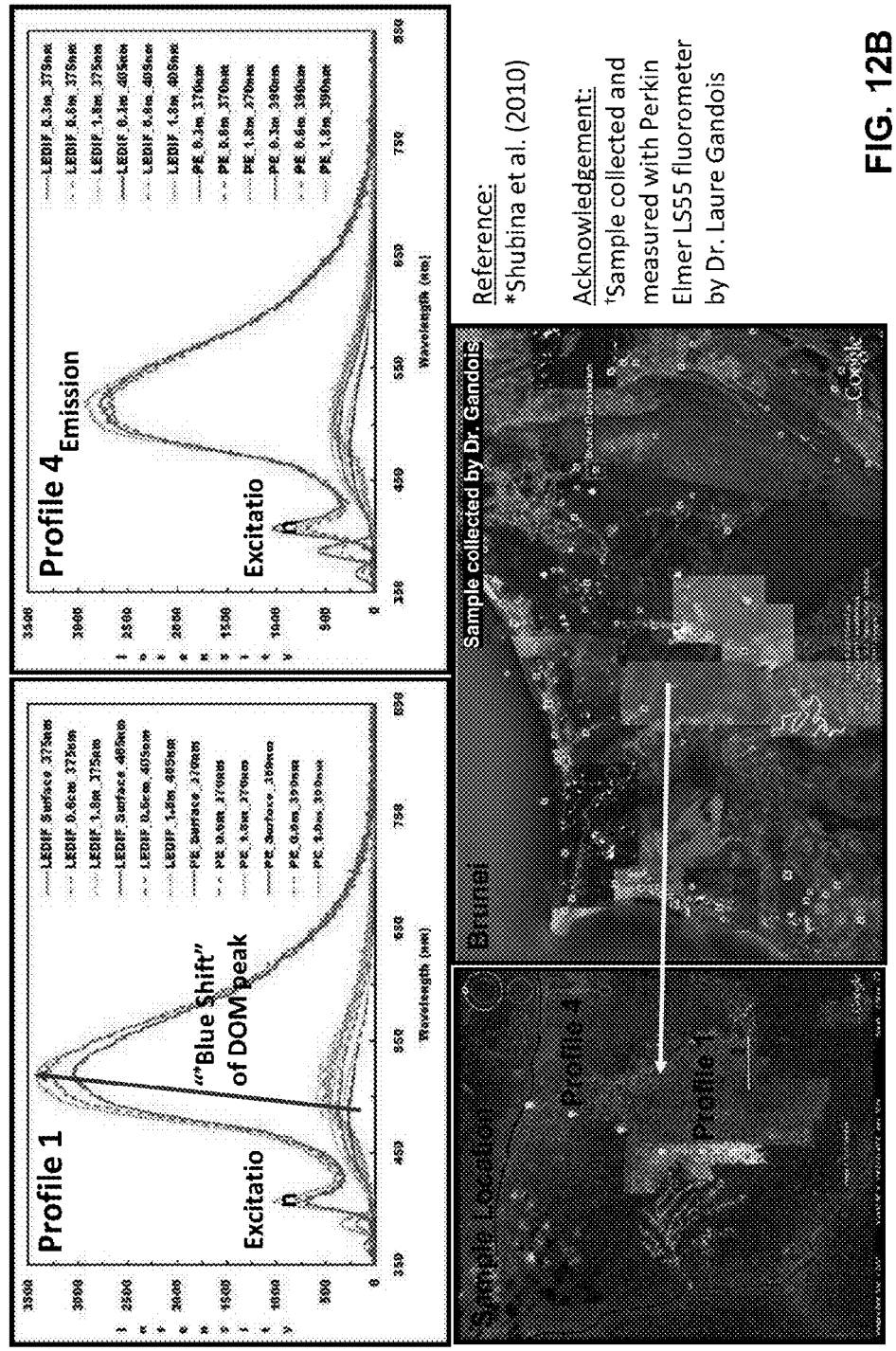
FIG. 12B shows a typical emission spectrum of a field sample obtained from a peatland in Brunei using a LEDIF sensor in accordance with an embodiment of the present disclosure.

FIG. 12B shows a typical emission spectrum of a field sample obtained from a peatland in Brunei (0.2 nm filtered peatland sample) by way of a LEDIF sensor in accordance with an embodiment of the present disclosure. After accounting for the "blue shift" effect of humic materials in the field sample, the maximum percent difference between the two sensors is 2.6%, which shows very good agreement despite humic materials having a very broad fluorescence peak. (II)

Figure 13:
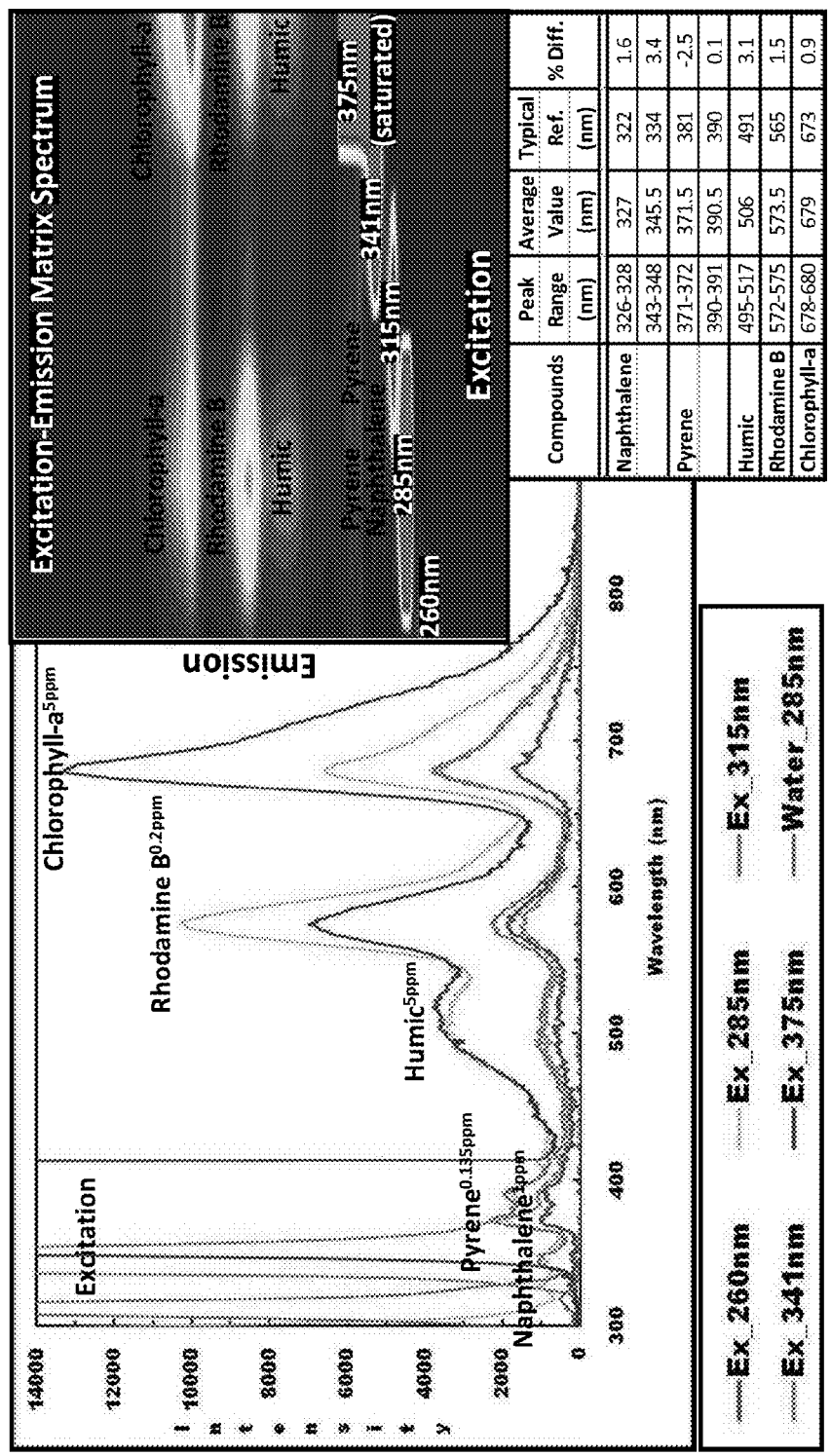
FIG. 13 shows a typical emission spectrum and Excitation-Emission Matrix (EEM) spectrum of a complex mixture, for testing the capabilities of a LEDIF sensor in accordance with an embodiment of the present disclosure relative to detecting and identifying multiple compounds.

FIG. 13 shows a typical emission spectrum and Excitation-Emission Matrix (EEM) spectrum of a complex mixture, specifically, an aqueous mixture of 5 ppm Chlorophyll a, 0.2 ppm Rhodamine B, 5 ppm Humic, 0.135 ppm Pyrene, and 1 ppm Napthalene, for testing the capabilities of a LEDIF sensor in accordance with an embodiment of the present disclosure with respect to detecting and identifying multiple compounds. The sensor can identify the peaks of each chemical in the mixture, with very good agreement to the typical published peak of any given single chemical. Note that the comparison data were mostly taken from PhotoChemCad, and that such data are often for compounds that have been dissolved in a different solvent (e.g., Naphthalene in Cyclohexane) that may contribute to the small percent difference in reported peaks. The multi-excitation of LEDIF makes the construction of in-situ EEM possible.

Figure 14:
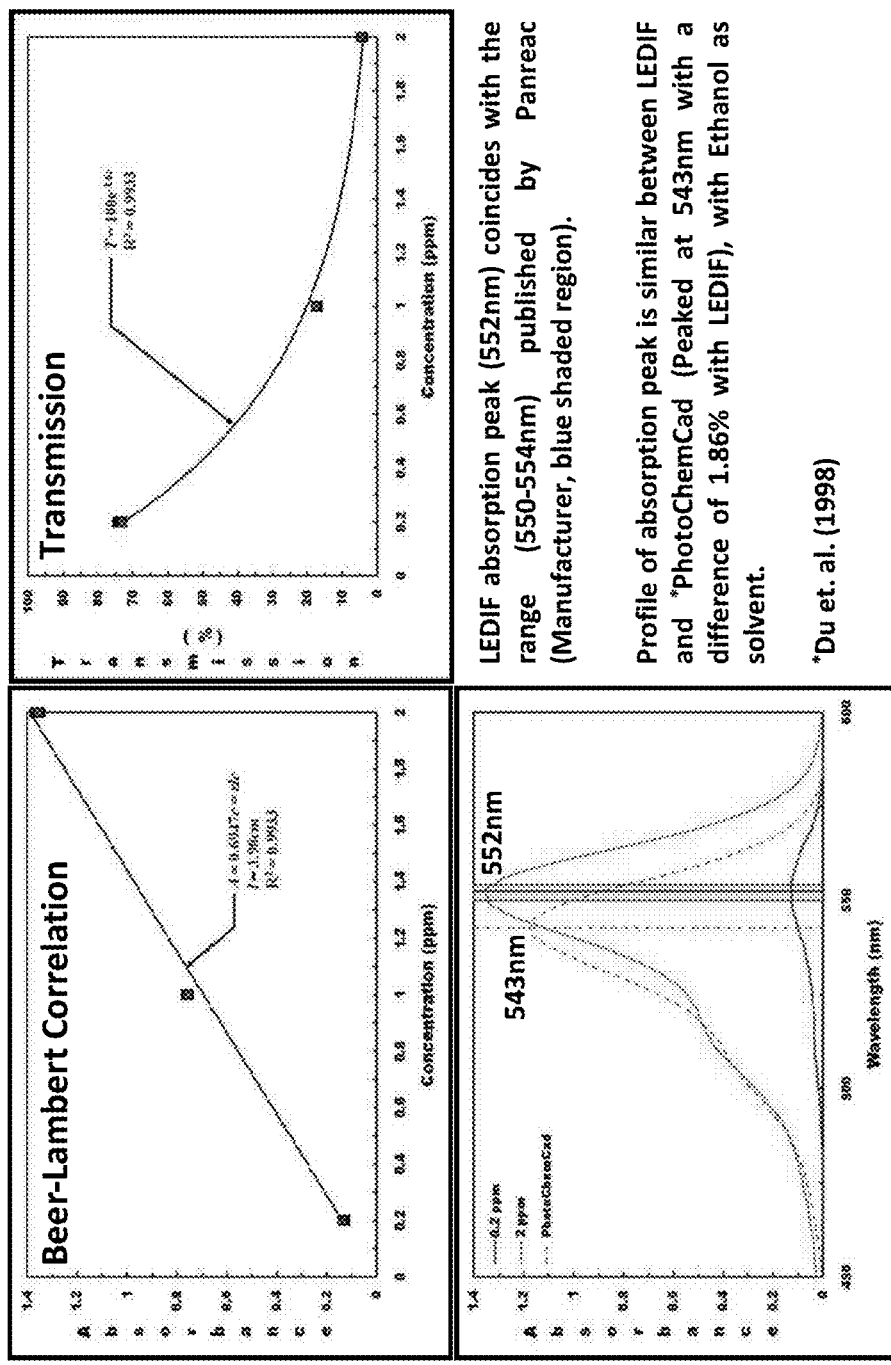
FIG. 14 shows a typical absorbance spectrum, Beer-Lambert Correlation, and Transmission measurements of a LEDIF sensor in accordance with an embodiment of the disclosure for Rhodamine B.

FIG. 14 shows a typical absorbance spectrum, Beer-Lambert Correlation, and Transmission measurements of a LEDIF sensor in accordance with an embodiment of the disclosure for Rhodamine B. The absorbance peak measured by a LEDIF sensor coincided with the measurement reported by the manufacturer (Panreac). The absorbance peak of Rhodamine B dissolved in ethanol reported by PhotoChemCad shows a very similar peak and profile to the one reported by LEDIF. The LEDIF sensor shows that 2 ppm Rhodamine B still falls onto the Beer-Lambert correlation.

Figure 15:
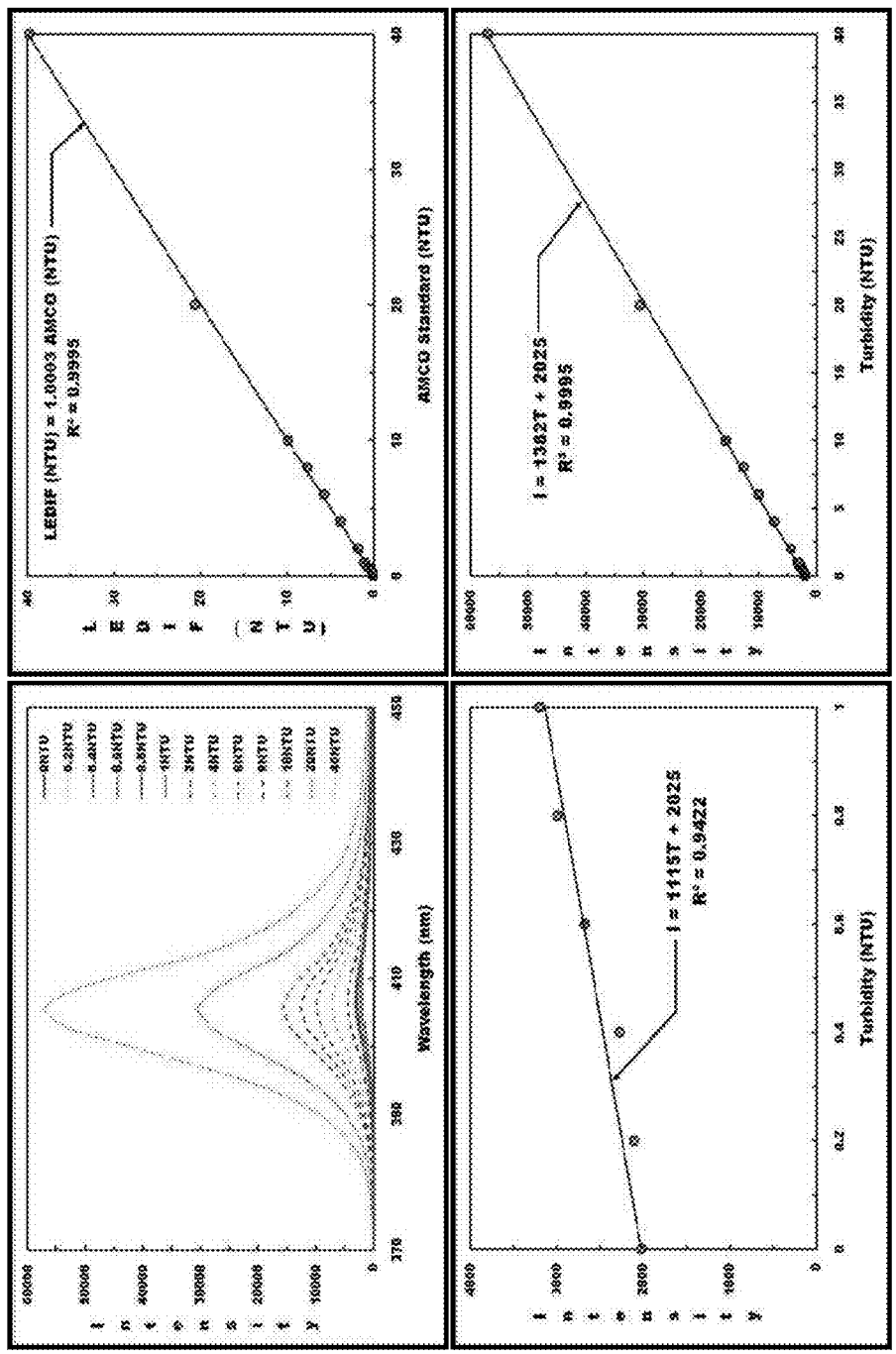
FIG. 15 shows a typical linear calibration curve for turbidity measurement by a LEDIF sensor in accordance with an embodiment of the present disclosure.

FIG. 15 shows a typical linear calibration curve for turbidity measurement by a LEDIF sensor in accordance with an embodiment of the present disclosure (IT=200 ms, and $\lambda_{Ex}$=405 nm). The LEDIF sensor shows turbidity measurements as low as 0.1 NTU can be measured, thus demonstrating it's application in evaluating processed drinking water (typical range<1 NTU). The range of 40 NTU is not the limitation of the LEDIF Sensor but rather the saturation point of 405 nm excitation wavelength at 200 ms. By either calibrating with a lower integration time and/or with a different LEDs, the range can be extended. Based on the minimum accessible integration time of 3.8 ms with the present spectrometer and the multi-excitation capabilities, the limitation will most likely arises from the liquid sample rather than from the LEDIF sensor.

Aspects of particular embodiments of the present disclosure address at least one aspect, problem, limitation, and/or disadvantage associated with exiting systems, apparatuses, circuits, and/or techniques for fluid sensing or characterization. While features, aspects, and/or advantages associated with certain embodiments have been described in the disclosure, other embodiments may also exhibit such features, aspects, and/or advantages, and not all embodiments need necessarily exhibit such features, aspects, and/or advantages to fall within the scope of the disclosure. It will be appreciated by a person of ordinary skill in the art that several of the above-disclosed systems, apparatuses, components, processes, or alternatives thereof, may be desirably combined into other different systems, apparatuses, components, processes, and/or applications. In addition, various modifications, alterations, and/or improvements (e.g., the inclusion of particular optical filter elements) can be made to various embodiments by a person of ordinary skill in the relevant art. Embodiments described in detail herein, modifications/variations thereto, and other embodiment modifications/variations are encompassed by the present disclosure and the scope of the following claims.

The invention claimed is:

1. An optical flowcell assembly comprising:
 a housing having an axial extent, a transverse extent, a periphery, and an internal channel having a length extending along a portion of the housing's axial extent, parallel to an optical signal detection axis of the flowcell assembly;
 at least one fluid inlet configured for fluid communication with the internal channel;
 at least one fluid outlet configured for fluid communication with the internal channel;
 a plurality of transverse optical junctions configured for directing optical signals into the internal channel along an optical signal propagation path that is offset from the flowcell assembly's optical signal detection axis; and
 at least one axial optical junction configured for receiving optical signals propagating from the internal channel to the at least one axial optical junction.

2. The optical flowcell assembly of claim 1, wherein the plurality of transverse optical junctions is configured for directing optical signals into the internal channel along an optical signal propagation path that is substantially transverse to the flowcell assembly's optical signal detection axis.

3. The optical flowcell assembly of claim 1, wherein the plurality of transverse optical junctions is configured for optical coupling to a plurality of source optical signal modules.

4. The optical flowcell assembly of claim 3, wherein the plurality of transverse optical junctions comprises a first set of transverse optical junctions disposed at a first position relative to the housing's axial extent.

5. The optical flowcell assembly of claim 4, wherein the plurality of transverse optical junctions further comprises a second set of transverse optical junctions disposed at a second position relative to the housing's axial extent, the first position and the second position spatially offset from each other.

6. The optical flowcell assembly of claim 1, further comprising an axial optical junction configured for directing optical signals into the internal channel along an optical signal propagation path that is substantially parallel to the flowcell assembly's optical signal detection axis.

7. The optical flowcell assembly of claim 1, further comprising a plurality of source optical signal modules, each source optical signal module within the plurality of optical signal modules one of coupled to and carrying one of a set of LEDs and a set of semiconductor lasers.

8. The optical flowcell assembly of claim 1, wherein each source optical signal module carries one of a single LED and a single semiconductor laser.

9. The optical flowcell assembly of claim 8, wherein each source optical signal module carries one of a single LED configured for outputting optical signals having a single optical center wavelength and a single LED configured for outputting optical signals having multiple distinct optical center wavelengths.

10. The optical flowcell assembly of claim 1, further comprising a plurality of source optical signal modules configured for outputting optical signals having a plurality of distinct optical center wavelengths.

11. The optical flowcell assembly of claim 10, wherein each source optical signal module within the plurality of source optical signal modules is configured for outputting optical signals having a distinct optical center wavelength relative to optical signals output by each other source optical signal module within the plurality of source optical signal modules.

12. The optical flowcell assembly of claim 1, further comprising a set of optical fibers optically coupled to the at least one axial optical junction.

13. The optical flowcell assembly of claim 1, wherein the optical flowcell assembly is configured for enabling at least two of fluorescence spectroscopy measurements, absorption spectroscopy measurements, and turbidity measurements.

14. The optical flowcell assembly of claim 1, wherein at least one of the plurality of transverse optical junctions and the at least one axial optical junction includes a first portion of a standard optical connector.

15. The optical flowcell assembly of claim 14, wherein at least one of the plurality of transverse optical junctions and the at least one axial optical junction includes a first portion of an SMA-type optical connector.

16. The optical flowcell assembly of claim 1, wherein the optical flowcell assembly is sized and dimensioned for deployment on a platform comprising one of a Remotely Operated Vehicle (ROV), an Autonomous Underwater Vehicle (AUV), an Autonomous Surface Vehicle (ASV), a buoy, and a water distribution network, and wherein the optical flowcell assembly facilitates optical spectroscopy measurements by the platform.

17. A source optical signal module optically couplable to an optical flowcell of an optical spectroscopy system, the source optical signal module having an optical axis and comprising:
 a first portion of an optical connector aligned relative to the optical axis of the source optical signal module and configured for mating engagement with a corresponding second portion of an optical connector separate from the source optical signal module;
 a housing having an axial extent, an outer cross-sectional area, and an inner cross-sectional area;
 a set of optical signal sources comprising one of an LED and a semiconductor laser carried internal to the housing, the set of optical signal sources configured to direct optical signals along the optical axis of the source optical signal module; and
 a set of optical path tuning elements carried internal to the housing and disposed between an optical signal source within the set of optical signal sources and the first portion of the optical connector, the set of optical path tuning elements comprising at least one of a set of lens elements and a set of spacer elements, each optical path tuning element within the set of optical path tuning elements having a cross-sectional area that is transverse to the optical axis of the source optical signal module, each optical path tuning element within the set of optical path tuning elements configured for selective adjustment of an optical path length corresponding to the set of optical signal sources relative to an optical spectroscopy measurement location within the optical flowcell.

18. The source optical signal module of claim 17, wherein the set of optical signal sources comprises one of a single LED and a single semiconductor laser.

19. The source optical signal module of claim 17, wherein the first portion of the optical signal connector corresponds to an SMA-type optical connector.

20. The source optical signal module of claim 17, wherein the housing has an internal diameter that less than approximately 3 times a cross-sectional area of a package corresponding to one of an LED and a semiconductor laser.

21. A spectroscopy system comprising:
a flowcell assembly having an axial extent, the flowcell assembly comprising:
a fluid inlet structure configured for receiving a fluid;
a fluid outlet structure configured for outputting a fluid;
a channel internal to the flowcell, the channel having a longitudinal extent configured for providing a spectroscopy measurement region along a fluid communication path between the fluid inlet structure and the fluid outlet structure;
a set of transverse optical junctions configured for directing optical signals into the channel substantially transverse to the longitudinal extent of the channel; and
an axial optical junction configured for receiving optical signals propagating away from the spectroscopy measurement region in a direction substantially parallel to the longitudinal extent of the channel;
a set of source optical signal modules physically and optically coupled to the flowcell assembly by way of a set of miniature optical connectors;
an emission collection assembly comprising a set of optical fibers optically coupled to the flowcell assembly; and
a miniature spectrophotometer optically coupled to the emission collection assembly.

22. The spectroscopy system of claim 21, wherein the spectroscopy system is configured for performing in-situ real-time spectroscopy measurements by way of directing optical signals provided by the set of source optical signal modules into the optical flowcell assembly's spectroscopy measurement region, capturing optical signals propagating toward the axial optical junction, and providing captured optical signals to the spectrophotometer.

23. The spectroscopy system of claim 21, wherein the spectroscopy system is configured for making spectroscopy measurements by simultaneously directing a plurality of optical excitation signals provided by a plurality source optical signal modules within the set of optical signal source modules into the optical flowcell assembly's spectroscopy measurement region, capturing optical emission signals corresponding to the plurality of optical excitation signals, and providing the captured optical emission signals to the spectrophotometer.

24. The spectroscopy system of claim 21, wherein the spectroscopy system is configured for performing at least two of fluorescence spectroscopy measurements, absorption spectroscopy measurements, and turbidity measurements.

25. The spectroscopy system of claim 21, wherein the spectroscopy system is configured for excitation—emission matrix spectroscopy.

26. The spectroscopy system of claim 21, further comprising a flow transportation manifold coupled to the optical flowcell assembly, the flow transportation manifold configured for in-situ real-time capture of fluid samples from a fluid environment and return of captured fluid samples to the fluid environment.

27. The spectroscopy system of claim 21, wherein the spectroscopy system excludes a pump configured for transferring fluid into the optical flowcell assembly.

28. The spectroscopy system of claim 21, wherein the spectroscopy system is deployable as a substantially self-contained unit on a plurality of platforms configured for at least partial exposure to fluid environments, the plurality of platforms comprising an ROV, an AUV, an ASV, a bouy, and a water distribution network.

29. The spectroscopy system of claim 21, further comprising:
an instruction processing device configured for executing program instruction sets; and
a memory coupled to the instruction processing device.

30. The spectroscopy system of claim 29, further comprising a software user interface configured for the generation of program scripts as text files specifying a set of commands written in accordance with a scripting language.

31. A method for performing optical spectroscopy measurements by way of a substantially self-contained optical spectroscopy system configured for in-situ real-time optical spectroscopy measurements, the method comprising:
deploying at least a portion of the substantially self-contained spectroscopy system in-situ within a fluid environment;
receiving a fluid sample within an internal channel of an optical flowcell assembly of the spectroscopy system; and
performing excitation—emission matrix spectroscopy measurements by way of:
energizing one of a set of LEDs and a set of semiconductor lasers carried by the spectroscopy system to generate a plurality optical excitation signals, each optical excitation signal within the plurality of optical excitation signals having a distinct optical center wavelength;
directing the plurality of optical excitation signals into the internal channel of the flowcell assembly;
detecting a set of optical emission signals corresponding to the plurality optical excitation signals directed into the internal channel of the flowcell; and
performing a set of fluorescence spectroscopy measurements.

32. The method of claim 31, wherein directing the plurality of optical excitation signals into the internal channel of the optical flowcell assembly comprises simultaneously directing the plurality of optical excitation signals into the internal channel of the flowcell assembly.

* * * * *